United States Patent
Guarnieri et al.

(10) Patent No.: US 11,718,857 B2
(45) Date of Patent: Aug. 8, 2023

(54) BROAD HOST RANGE GENETIC TOOLS FOR ENGINEERING MICROALGAE

(71) Applicant: Alliance for Sustainable Energy, LLC, Golden, CO (US)

(72) Inventors: Michael T. Guarnieri, Denver, CO (US); Jeffrey George Linger, Denver, CO (US); Lukas Royce Dahlin, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 340 days.

(21) Appl. No.: 16/989,549

(22) Filed: Aug. 10, 2020

(65) Prior Publication Data

US 2021/0071187 A1    Mar. 11, 2021

Related U.S. Application Data

(60) Provisional application No. 62/884,918, filed on Aug. 9, 2019.

(51) Int. Cl.
*C12N 15/82* (2006.01)
*C12N 1/12* (2006.01)

(52) U.S. Cl.
CPC ........... *C12N 15/8209* (2013.01); *C12N 1/12* (2013.01)

(58) Field of Classification Search
CPC .. C12N 1/12; C12N 15/8209; C12N 15/8214; C12N 15/79; C12N 15/8247; C12N 15/8216; C12N 15/8213; C12N 15/902; C12N 15/8201; C12N 15/90
See application file for complete search history.

(56) References Cited

U.S. PATENT DOCUMENTS

2012/0252054 A1* 10/2012 Botsch ................... C12N 15/79
                                                                 435/257.2
2017/0152520 A1*  6/2017 Moellering ........ C12N 15/8218

OTHER PUBLICATIONS

Remacle, Claire, et al. "High-efficiency biolistic transformation of Chlamydomonas mitochondria can be used to insert mutations in complex I genes." Proceedings of the National Academy of Sciences 103.12 (2006): 4771-4776. (Year: 2006).*
Fajardo, Carlos, et al. "Advances and challenges in genetic engineering of microalgae." Reviews in Aquaculture 12.1 (2020): 365-381. (Year: 2020).*
Dahlin et al., "Development of a high-productivity, halophilic, thermotolerant microalga Picochlorum renovo", Communications Biology, 2019, vol. 2, No. 388, pp. 1-9.
Henard et al., "Muconic Acid Production from Methane using Methanotrophic Biocatalysts", Green Chemistry, 2019, vol. 21, pp. 6731-6737.
Pandeya et al., "Selective fertilization with phosphite allows unhindered growth of cotton plants expressing the ptxD gene while suppressing weeds", PNAS, 2018, vol. 115, No. 29, pp. E6946-E6955.

* cited by examiner

*Primary Examiner* — Weihua Fan
(74) *Attorney, Agent, or Firm* — Alexandra M. Hall; Sam J. Barkley

(57) ABSTRACT

Disclosed herein are a suite of genetic tools suitable for engineering both the nucleus and chloroplast in diverse microalgae.

8 Claims, 8 Drawing Sheets

Specification includes a Sequence Listing.

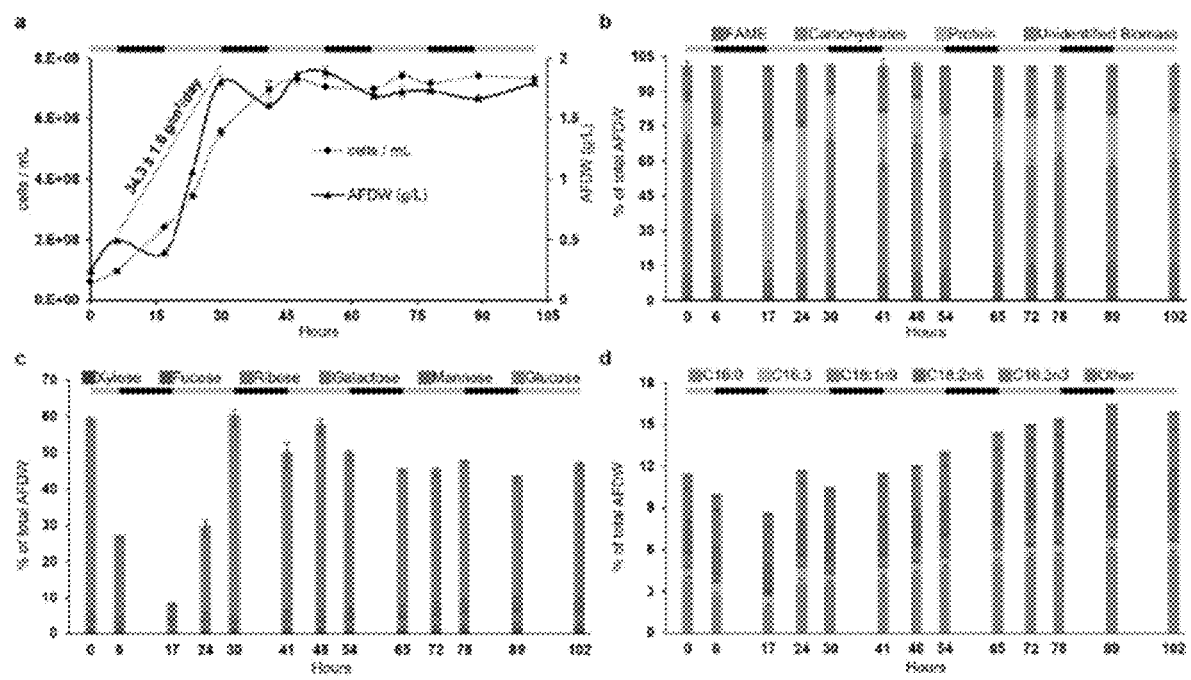
FIGs. 2a, 2b, 2c, and 2d

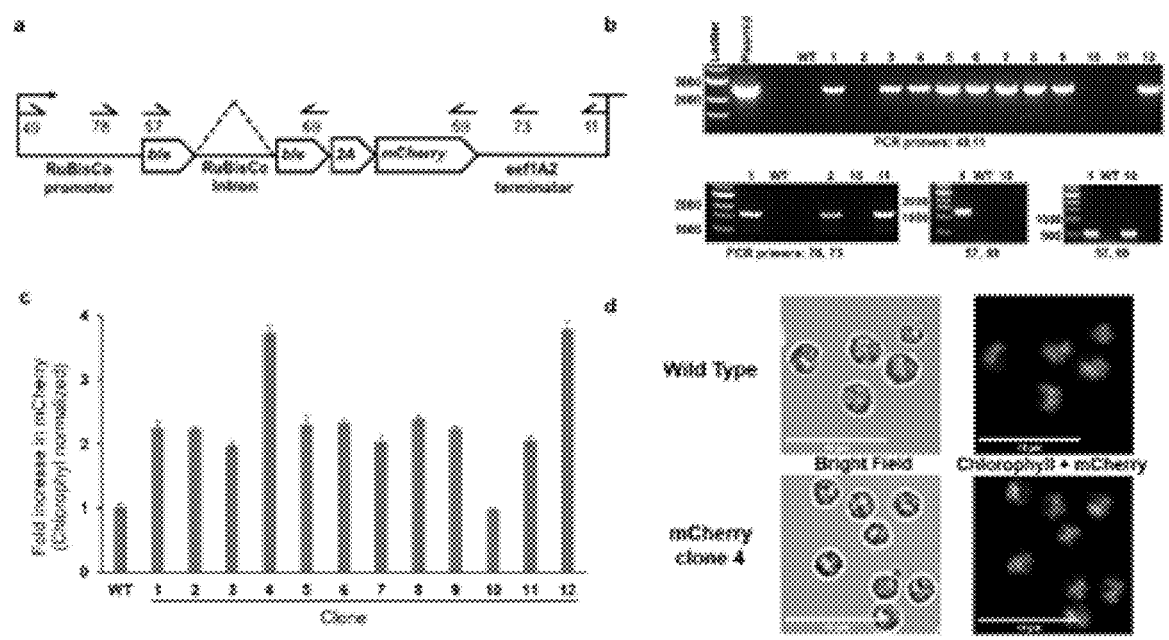
FIGs. 7a, 7b, 7c, and 7d

SEQUENCE LISTING

```
<160> NUMBER OF SEQ ID NOS: 29

<210> SEQ ID NO 1
<211> LENGTH: 650
<212> TYPE: DNA
<213> ORGANISM: Picochlorum renovo

<400> SEQUENCE: 1
tggatttcct caaggatgaa gtgtcacagc aatttgaaaa agtagaaaaa attgccaatg      60
tgttggagca gatagagaaa aaacaaaaga ctctgcgcta tcgccaggat aaagtgcagt     120
ttatggcatc taatataaat gacagagtga aattattggc agaatgcatt gggcggttcc     180
tcaaccagca tctgaagctg agaagcactt ccaacaccat gaactgccca tgctggagtc     240
aaacacggca tcattagctc aagaggtagc tatgctccga tcccaggcgc aagcagtaaa     300
acaatcaggg aaagtacaac agtcacatgg ctctgcttcc aaagcctcac caagtgattt     360
gcgaagaatc agggaaatgc tatcagaaca cgacaccatc attagagata tgtgccgaaa     420
ggtgcgagcc atcgagtcca gtgtataggg ttgtgtcttc ctgccgtgtc tgaagaggat     480
gtaaaaaaag tgccctgatt tttatatcgt aattacgacc gaagttccgt ttccatgcat     540
cgacgaagca tgcttcatta tcctgataaa cacgtgaggc atgcgcctca cctgcacaat     600
ataattcagt ttttttatct ttgaaaactt actacaaaca aattaacaaa                650

<210> SEQ ID NO 2
<211> LENGTH: 650
<212> TYPE: DNA
<213> ORGANISM: Picochlorum renovo

<400> SEQUENCE: 2
ttattttaga atgaattcga ttgctctgaa gacatcgctc gctggatgct caaagagggt      60
atccatcccc atcggcaccc acagaacagc accaaggctc tgtactacta ctactacaag     120
aacaaggacc tgtctttact ctggtaacgg tagcaccggg ggtgatgatg tatctacacc     180
tgcagtagca attgcagtcg caggccttgc ttatccgccc atcgtcttct ggtcagagta     240
caccttggca acgactggaa gtggccttcc tcctggccca ggtggagcat tgggtgcagc     300
agagggtatt tcataccttg caagcgtggg gattgtcgca tggtctctca agacaaaggt     360
tcagactggg agtggattac cagcgggacc cagtggtctc gtgggtgcag cagagggcgt     420
ttcatacctt gcagtgcttg gtggattgat tgccgcaggc gtgtccacca tgtcgtaaag     480
aagaaagtcg gaataggatt ccaattcccg aattagtttg accaccattg tgggcgcatg     540
tgcggctgac tccctcaagt tctcatgtcc acaccgaaa  tagccctctt aaaaacatat     600
attgttagtt ataaactcag tgttgttaac tatctctaaa aacatttaaa                650

<210> SEQ ID NO 3
<211> LENGTH: 650
<212> TYPE: DNA
<213> ORGANISM: Picochlorum renovo
```

<400> SEQUENCE: 3

```
gtgcagaata catacacaac cttcgatgat gatgatggaa gaaggtgata gtgtagcatg    60
ggaaggggag acgtacgagc cggacaatgt catttgtgga gacgggagaa ctgcgcctga   120
tggtcacatg ctcaagttca ttcaacacat ggcagccatc cctgatcaat gtctgaggct   180
cctatacacg gctcgcgaca ggctcgctgc atttagaatc aaacaaagaa ttaattgaaa   240
atcaggcaac attgtccatc ctgcaatgcc ccacgagcat gcgttgccca agtaacctcc   300
ccactcattg cagcactgat cgagtccttg gatatggttc cagcaacaga ccacttccgg   360
tcacctccct cctcctggga atgggccatc atagaaatac ggatatgtag caaactttgt   420
acgcatgaaa atgatcgaga caaggccata ccgatcgaag aagctgtcaa cactatgggg   480
aagcttgaac ctttgcctgg gtcaaaagga ttccacctcg tcccgaatta gtttggacac   540
aatcgcctgg aacgtccaaa agataacag caaaatctcc acattcctcc ttatcgatta    600
tcctactttt accccttcc atcttggcta tttccttgga ttaatagaaa              650
```

```
<210> SEQ ID NO 4
<211> LENGTH: 470
<212> TYPE: DNA
<213> ORGANISM: Picochlorum renovo
```

<400> SEQUENCE: 4

```
gatgttgact gctatgtgat gagatggccg atcaaattgt cagtggtggt gcttttgcat    60
caacatggat tctggttggc ttgatcaata attattttgc atagtttttt acacaacatc   120
tattattctt gtaatatggg tcagaaagcc ttggtttaca cagatgcact gccatcacca   180
tcatcatcat catcatcagt ggtgcagtca acagattctt ctggcaacgt tggccgactg   240
atttcatcga ttccctttttg aatttatcaa ccaattgctt catatacgat ggtgaacatc   300
tgttaacaag ctcttttgga tacatctggc aaatgctcat catggaatga tgcaatgcag   360
gattcttctc ccctgtatgt ttagaataga atagaatatg taacaagatg aagcaacgga   420
caacaactgg aagcatagta tggaaatgta tgtaccttgg gctatgagtg              470
```

```
<210> SEQ ID NO 5
<211> LENGTH: 134
<212> TYPE: DNA
<213> ORGANISM: Picochlorum renovo
```

<400> SEQUENCE: 5

```
gtatgattta catgtttatt gaagcacagt ttatgacacg cgtgagctcc aatgcgcgac    60
tttccaagtc agcgcctcgg tgcactccgc caatgtgaac aaggcgctaa ccctcgttgt   120
ttgtcattat gcag                                                    134
```

```
<210> SEQ ID NO 6
<211> LENGTH: 161
<212> TYPE: DNA
<213> ORGANISM: Picochlorum renovo
```

<400> SEQUENCE: 6

```
gtacgttttg gtggcatcag aggctgcgca cagatcagag gcggccttcg taactgtcct    60
tggacgcctg tggcggtagc atgcatgcat gataatgttt tataattatg aatttaatgc   120
acatggtata tatactgact gaattctgtg tacccatgca g                      161
```

<210> SEQ ID NO 7

```
<211> LENGTH: 355
<212> TYPE: DNA
<213> ORGANISM: Picochlorum renovo

<400> SEQUENCE: 7
gtacgtagga agtcttatca agactgttga tgaagcggat gtcaactcgc tggaattctg      60
cgtcttttgg ccgatggctt ccatgtagag tagtattttg tttattattt atatcatgat     120
ttgatcgcgt atggttatgg gatattattg agtgtgtgag tgtcaccacc agcgaggata     180
cggcgagtct aggatggggc tcggattctg tgggcgatgg gacccaacga atcagtgttc     240
cagacaagtg tattcgtagg gttggggaat gagaaggcta ccaaatacat acgtagctca     300
agatacgggt tatgaaacaa ggcattgctc tgacatgaat gttgttggtg tacag         355

<210> SEQ ID NO 8
<211> LENGTH: 387
<212> TYPE: DNA
<213> ORGANISM: Picochlorum renovo

<400> SEQUENCE: 8
atggccagga tggccaagtt gacgtcagcc gttccagttc tcacagccag ggacgtggcc      60
ggtgctgttg agttctggac agatcggctt ggtttctccc gagatttcgt ggaagatgac     120
tttgcaggcg tagttagaga tgacgtgacg ctgtttatct ctgccgtgca ggatcaggac     180
caagtggtgc ccgacaatac actggcttgg gtctgggtgc gtgggctgga tgagttatat     240
gccgagtgga gcgaagttgt ctccactaat tttcgtgatg catctggtcc agcaatgacg     300
gagattggag aacagccatg ggggcgcgag tttgcattga gagatccagc gggcaactgt     360
gtacattttg ttgcggagga acaggat                                        387

<210> SEQ ID NO 9
<211> LENGTH: 120
<212> TYPE: DNA
<213> ORGANISM: Picochlorum renovo

<400> SEQUENCE: 9
ctgttggcca ttcatccaac tgaggctcgc cataagcaga aaattgtggc acccgtcaag      60
cagactttga atttcgatct tcttaaattg gctggcgacg tggaatctaa tccaggacct     120

<210> SEQ ID NO 10
<211> LENGTH: 711
<212> TYPE: DNA
<213> ORGANISM: Picochlorum renovo

<400> SEQUENCE: 10
atggtcagta agggagagga agacaatatg gcaatcatca aggaatttat gagattcaaa      60
gtgcatatgg agggtagtgt aaacgggcac gaatttgaaa ttgagggcga ggggaaggt     120 agaccttacg aggggacaca gacagctaaa cttaaggtca ctaagggcgg tcctctacca     180
tttgcctggg acattctttc gccgcaattc atgtatggca gcaaggctta tgttaaacat     240
cctgccgata tcccagatta cctcaagctt tctttcccag agggattcaa gtgggagcga     300
gtgatgaatt ttgaagacgg cggtgttgtc actgtgacgc aggactcttc cttgcaggac     360
ggagaattca tctataaagt gaagctcaga ggcacaaatt ttccttcaga tggtcctgtg     420
atgcagaaaa aaacaatggg gtggaggcg tcctcagaga ggatgtatcc agaggatgga     480
gcactcaagg gggaaattaa acagagatta agctgaaag acgaggcca ttatgatgct     540 gaagtgaaaa ctacctacaa agcgaaaaag cctgtgcagc ttcctggagc atataatgtg     600
```

```
aacataaaat tggatattac ttcgcacaat gaggattata ctattgtcga acagtatgaa    660
cgggcagaag aagacactc tacgggcggc atggatgagc tttacaaata a              711
```

<210> SEQ ID NO 11
<211> LENGTH: 795
<212> TYPE: DNA
<213> ORGANISM: Picochlorum renovo

<400> SEQUENCE: 11

```
atgatcgagc aagacggtct tcatgcgggg agtcctgcgg cctgggtgga gcgactttt     60 ggttacgatt gggctcagca acaatagga tgttcagacg cagcagtttt tcggctctcg    120
gcccagggta ggcctgtact tttcgtgaaa acagatttga gcggtgctct gaacgaactt   180
caagatgaag ccgctcgcct cagctggtta gcaacaacgg gggtcccgtg cgccgctgtg   240
ttggacgtgg tgaccgaggc gggtagggat tggttgttac tgggagaggt gcccggacag   300
gatttactta gctcgcatct cgcaccagca gagaaggtaa gtattatggc agacgctatg   360
agacgtttgc atacgttgga tcctgcaaca tgcccgttcg atcaccaagc caaacatcga   420
attgaacgtg cacgaacaag aatggaggca gggcttgttg accaagacga cttagatgag   480
gaacaccagg gtttggcccc cgcagagtta tttgcaaggt tgaaagcatc catgcccgat   540
ggggaagatc tagtcgtgac gcatgggac gcttgtttgc ctaatataat ggtagaaaat    600
ggacggttct ccggtttcat agattgtggg cgtttaggtg tggcggatcg ttatcaagat   660
atagcccttg ccacaaggga tatcgcagag gaactgggag gagaatgggc agatagattt   720
ttggttctct atgggattgc ggcaccagat tcacagcgaa ttgcatttta caggttactg   780
gacgagtttt tttaa                                                    795
```

<210> SEQ ID NO 12
<211> LENGTH: 1000
<212> TYPE: DNA
<213> ORGANISM: Picochlorum renovo

<400> SEQUENCE: 12

```
gcgagggtag caaatgggat tagataccc agtagtcctc gccgtaaacg atggatacta     60
ggtgttggat gggttcaaat cattcagtac cgtagctaac gcgtgaagta tcccgcctgg   120
ggagtatgct cgcaagagtg aaactcaaag gaattgacgg gggcccgcac aagcggtgga   180
gcatgtggtt taattcgatg caacgcgaag aaccttacca gggcttgaca tgtcactttt   240
ttcttgaaag agaaagttcc cgagtgaaca caggtggtgc atggctgtcg tcagctcgtg   300
tcttgagatg ttgggttaag tcccgcaacg agcgcaaccc ttattctgtg ttgctatttg   360
ataggaaact cagaagactg ccggtgataa gccggaggaa ggtgaggatg acgtcaagtc   420
agcatgcccc ttacgccctg ggctacacac gtgctacaat ggccgggaca agagatgca    480 atctcgcgag agcaagctaa cctcaaaaac ccggtcttag ttcggattgt aggctgaaac   540
tcgcctacat gaagctggaa tcgctagtaa tcgcaggtca gccatactgc ggtgaatacg   600
ttcccgggcc ttgtacacac cgcccgtcac accatggaag ctggctatgc ccaaagtcgt   660 tacccccaacc ttttggaggg ggacgcctaa ggcagagcta gtgactaggg tgaagtcgta  720
acaaggtagc cgtactggaa ggtgcggctg gatcacctcc ttaaaaagga aataaataa    780 aaatacaatt ttgtatttaa aagttcatat catctgttat ccctaaaaat ctagggatac   840
aggccgatgt acggcctggg ctaatagccc acttttcga  ttttttgaaa aacaaatggg   900
```

```
ctattagctc agttggttag agcgcacgcc tgataagcgt gaggtcactg gttcaactcc    960
agtatagccc accagataga tatttatcta taaagaattg                         1000
```

<210> SEQ ID NO 13
<211> LENGTH: 1000
<212> TYPE: DNA
<213> ORGANISM: Picochlorum renovo

<400> SEQUENCE: 13

```
ttaaaaagtg ggtgaacttc atgatatttt tatcatgggg gtatagctca gttggtagag     60
cgctgccctt gcaaggcaga agtcagcggt tcgaatccgc ttatctccac catgttttc    120 tattgaaaat atggtaaaga attggtcaaa tgacttaaag catagggtgg atacctaggc   180
acctaaagac gatgaagggc gtggaaccga cgatacgctt cggggagctg aaacgagct    240 ttgatccgaa gattcccgaa tggggcaacc caataaacta tccactgaat tcataggtgg   300
aaaagagata acttagtgaa ctgaaacatc ttagtagcta aaggaagaga agcaaacgc    360 gattcccgga gtagtggcga gcgaaatggg aacagcctaa accaatattt tatattgggg   420
tcgtgggaaa acatgattta ctaagttaaa aacaatttaa atgaaacagc tgaatcctgt    480
accaaagaag gtaaaagtcc tgtaattgaa aaatttaatt ttaacttta acaactatgt    540 tagttatgtt tatcccgagt agcatgggac acgtgaaatc ccgtgtgaat cagcgaggac   600
cacctcgtaa ggctaaatac tcttaggtga ccgatagtga agtagtaccg tgagggaaag   660
gtgaaaagaa cccctgtagg ggagtgaaat agaacatgaa accctatgct gacaaacagt    720
gggaggtact tcaagtactg accgcgtacc tgttgaagaa tgggccggcg acttagaaag   780
agtggcaagg ttaaagacaa taatctggag ccagagcgaa agcaagtctg aatagggcga   840
gttaagtcac tttttctaga cccgaacccg ggtgatctaa ccatgaccag gatgaagctt    900
gggtaacacc acgtgaaggt ccgaaccgac tgatgttgaa aaatcagcgg atgagttgtg    960
gttagcggtg aaataccagt cgaactcgga gctagctggt                        1000
```

<210> SEQ ID NO 14
<211> LENGTH: 150
<212> TYPE: DNA
<213> ORGANISM: Picochlorum renovo

<400> SEQUENCE: 14

```
tagtcatatt aatttttact acatatatat attggtttgt taaaaaattt atattttcca     60
gttagattct ggaaaatatg atataaagag aggcagagtg gtttgacttt ttatcagaac   120
atgatacatt aatcaatgtg aaaaaatttc                                    150
```

<210> SEQ ID NO 15
<211> LENGTH: 15
<212> TYPE: DNA
<213> ORGANISM: Picochlorum renovo

<400> SEQUENCE: 15

```
aggaggttat aaaaa                                                     15
```

<210> SEQ ID NO 16
<211> LENGTH: 717
<212> TYPE: DNA
<213> ORGANISM: Picochlorum renovo

<400> SEQUENCE: 16

```
atgagcaaag gagaagaact tttcactgga gttgtcccaa ttcttgttga attagatggt     60
```

| | |
|---|---|
| gatgttaatg ggcacaaatt ttctgtccgt ggagagggtg aaggtgatgc tacaaacgga | 120 |
| aaactcaccc ttaaatttat ttgcactact ggaaaactac ctgttccatg ccaacactt | 180 |
| gtcactactc tgacctatgg tgttcaatgc ttttcccgtt atccggatca catgaaacgg | 240 |
| catgactttt tcaagagtgc catgcccgaa ggttatgtac aggaacgcac tatatctttc | 300 |
| aaagatgacg ggacctacaa gacgcgtgct gaagtcaagt ttgaaggtga taccctttgtt | 360 |
| aatcgtatcg agttaaaagg tattgatttt aagaagatg aaacattct cggacacaaa | 420 |
| ctcgagtaca actttaactc acacaatgta tacatcacgg cagacaaaca aaagaatgga | 480 |
| atcaaagcta acttcaaaat tcgccacaac gttgaagatg ttccgttca actagcagac | 540 |
| cattatcaac aaaatactcc aattggcgat ggccctgtcc ttttaccaga caaccattac | 600 |
| ctgtcgacac aatctgtcct ttcgaaagat cccaacgaaa agcgtgacca catggtcctt | 660 |
| cttgagtttg taactgctgc tgggattaca catggcatgg atgagctcta caaataa | 717 |

<210> SEQ ID NO 17
<211> LENGTH: 1260
<212> TYPE: DNA
<213> ORGANISM: Picochlorum renovo

<400> SEQUENCE: 17

| | |
|---|---|
| atgaggttcg aagaatgggt caaagataag catattcctt tcaaactgaa tcaccctgat | 60 |
| gataattacg atgattttaa gccattaaga aaaataattg gagatacccg agttgtagca | 120 |
| ttaggtgaaa attctcattt cataaaagaa ttttttttgt tacgacatac gcttttgcgt | 180 |
| tttttatcg aagacctcgg ttttactacg tttgcttttg aatttggttt tgctgagggt | 240 |
| caaatcatca ataactggat acatggacaa ggaactgacg atgaaatagg cagattctta | 300 |
| aaacacttct attatccaga agagctcaaa accacatttc tatggctaag ggagtacaat | 360 |
| aaagcagcaa aagaaaaaat cacatttctt ggcattgata tacccagaaa tggaggttca | 420 |
| tacttaccaa atatggagat agtgcatgac tttttttagaa cagcggataa agaagcacta | 480 |
| cacattatcg atgatgcatt taatattgca aaaaagattg attacttctc cacatcacag | 540 |
| gcagccttaa atttacatga gctaacagat tctgagaaat gccgtttaac tagccaatta | 600 |
| gcacgagtaa aagttcgcct tgaagctatg gctccaattc acattgaaaa atatgggatt | 660 |
| gataaatatg agacaattct gcattatgcc aacggtatga tatacttgga ctataacatt | 720 |
| caagctatgt cgggctttat ttcaggaggc ggaatgcagg gcgatatggg tgcaaaagac | 780 |
| aaatacatgg cagattctgt gctgtggcat ttaaaaaacc cacaaagtga gcagaaagtg | 840 |
| atagtagtag cacataatgc acatattcaa aaaacaccca ttctgtatga tggatttcta | 900 |
| agttgcctac caatgggcca aagacttaaa atgccattg tgatgatta tatgtcttta | 960 |
| ggtattactt cttatagtgg gcatactgca gccctctatc cggaagttga tacaaaatat | 1020 |
| ggttttcgag ttgataactt ccaactgcag gaaccaaatg aaggttctgt cgagaaagct | 1080 |
| atttctggtt gtggagttac taattctttt gtcttttta gaaatattcc tgaagattta | 1140 |
| caatccatcc cgaacatgat tcgatttgat tctatttaca tgaaagcaga acttgagaaa | 1200 |
| gcattcgatg gaatatttca aattgaaaag tcatctgtat ctgaggtcgt ttatgaataa | 1260 |

<210> SEQ ID NO 18
<211> LENGTH: 135
<212> TYPE: DNA
<213> ORGANISM: Picochlorum renovo -continued

<400> SEQUENCE: 18
aaaaaggaaa ataaataaaa atacaatttt gtatttaaaa gttcatatca tctgttatcc    60
ctaaaaatct agggatacag gccgatgtac ggcctgggct aatagcccac ttttcgatt    120 ttttgaaaaa caaat    135

<210> SEQ ID NO 19
<211> LENGTH: 33
<212> TYPE: DNA
<213> ORGANISM: Picochlorum renovo

<400> SEQUENCE: 19
cactcatagc ccaaggtaca tacatttcca tac    33

<210> SEQ ID NO 20
<211> LENGTH: 29
<212> TYPE: DNA
<213> ORGANISM: Picochlorum renovo

<400> SEQUENCE: 20
tggatttcct caaggatgaa gtgtcacag    29

<210> SEQ ID NO 21
<211> LENGTH: 21
<212> TYPE: DNA
<213> ORGANISM: Picochlorum renovo

<400> SEQUENCE: 21
atggccagga tggccaagtt g    21

<210> SEQ ID NO 22
<211> LENGTH: 27
<212> TYPE: DNA
<213> ORGANISM: Picochlorum renovo

<400> SEQUENCE: 22
ttatttgtaa agctcatcca tgccgcc    27

<210> SEQ ID NO 23
<211> LENGTH: 27
<212> TYPE: DNA
<213> ORGANISM: Picochlorum renovo

<400> SEQUENCE: 23
atcctgttcc tccgcaacaa aatgtac    27

<210> SEQ ID NO 24
<211> LENGTH: 28
<212> TYPE: DNA
<213> ORGANISM: Picochlorum renovo

<400> SEQUENCE: 24
accaaggctt tctgacccat attacaag    28

<210> SEQ ID NO 25
<211> LENGTH: 34
<212> TYPE: DNA
<213> ORGANISM: Picochlorum renovo

<400> SEQUENCE: 25
tttatatcgt aattacgacc gaagttccgt ttcc    34

```
<210> SEQ ID NO 26
<211> LENGTH: 25
<212> TYPE: DNA
<213> ORGANISM: Picochlorum renovo

<400> SEQUENCE: 26
tgggccgtaa ctgacactga gagac                                              25

<210> SEQ ID NO 27
<211> LENGTH: 34
<212> TYPE: DNA
<213> ORGANISM: Picochlorum renovo

<400> SEQUENCE: 27
caactccagt gaaaagttct tctcctttgc tcat                                    34

<210> SEQ ID NO 28
<211> LENGTH: 31
<212> TYPE: DNA
<213> ORGANISM: Picochlorum renovo

<400> SEQUENCE: 28
ccaactgcag gaaccaaatg aaggttctgt c                                       31

<210> SEQ ID NO 29
<211> LENGTH: 29
<212> TYPE: DNA
<213> ORGANISM: Picochlorum renovo

<400> SEQUENCE: 29
gtgctttacc cctagatagc cttgctgac                                          29
```

BROAD HOST RANGE GENETIC TOOLS FOR ENGINEERING MICROALGAE

CROSS REFERENCE TO RELATED APPLICATIONS

This application claims priority under 35 U.S.C. § 119 to U.S. provisional patent application No. 62/884,918 filed on 9 Aug. 2019, the contents of which are hereby incorporated in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

REFERENCE TO SEQUENCE LISTING

This application contains a Sequence Listing submitted as an electronic text file entitled "19-129_ST25.txt." having a size in bytes of 16 kb and created on Nov. 18, 2020. Pursuant to 37 CFR § 1.52(e)(5), the information contained in the above electronic file is hereby incorporated by reference in its entirety.

BACKGROUND

Microalgae are a source of renewable biomass and promising photosynthetic biocatalysts for the sustainable production of fuel and chemical intermediates. Importantly, they are also valuable model systems for fundamental investigation of mechanistic photobiology. These microbes possess a series of unique characteristics that make them well-suited for biotechnological applications, including year-round cultivation capacity in saline water on non-arable land, higher potential biofuel yields than terrestrial crops, and the ability to utilize $CO_2$ as a sole carbon source. Rising greenhouse gas emissions from anthropogenic sources has led to a resurgent interest in exploiting these organisms for concurrent $CO_2$ capture and renewable biocommodity production. However, at present, current model algal systems are not suitable for outdoor deployment, displaying low productivity under relevant environmental conditions (e.g. high light intensity, high temperature, seawater environments). Further, top candidate deployment systems display low genetic throughput, often requiring weeks to-months to generate and verify transgenic lines, which hinders fundamental mechanistic inquiry and metabolic engineering strategies in deployment-relevant microalgae.

Since its first classification in 2004, the genus *Picochlorum* has been recognized for its distinct characteristics of broad thermotolerance, salinity tolerance, compact genome architecture, fast doubling time, and resilience to high light intensity. An alga of the genus *Picochlorum* was recently shown to have the highest biomass productivity in a comparative analysis between a series of industrially relevant microalgae, underscoring this genera's deployment potential. However, to date, there are limited insights into *Picochlorum haloterance*, biosynthetic capacity, biomass characterization, and genetic tractability, hindering its development as a fundamental platform and for biotechnical applications.

SUMMARY

In an aspect, disclosed herein is a method for transforming algal chloroplasts. In an embodiment, the algal chloroplasts are from the genus *Picochlorum*. In an embodiment, the algal chloroplasts are from the genus *Scenedesmus* sp.

In an aspect, disclosed herein is a method for transforming algal mitochondria. In an embodiment, the algal mitochondria are from the genus *Picochlorum*. In an embodiment, the algal mitochondria are from the genus *Scenedesmus* sp.

In an aspect, disclosed herein is a method for transforming algal nuclei. In an embodiment, the algal nuclei are from the genus *Picochlorum*. In an embodiment, the algal nuclei are from the genus *Scenedesmus* sp.

DESCRIPTION OF THE DRAWINGS

FIGS. 2a, 2b, 2c, and 2d depict an overview of *P. renovo* productivity and associated biomass composition as a function of time. Alternating shaded bars depict the light-dark growth cycle. FIG. 2A shows growth curves as a function of ash-free dry weight (AFDW) (g/L) and cell density (cells/mL). Areal productivity is shown for hour 6 to 30, representing one light-dark cycle (day). FIG. 2B shows the biomass content of liquid (as fatty acid methyl ester, FAME), carbohydrate, protein, and the fraction of biomass not identified. FIG. 2C shows carbohydrate speciation via hydrolysis of biomass. FIG. 2D shows fatty acid speciation via fatty acid methyl ester analysis, representative of the lipid fraction of the biomass. All data points are an average of n=3 biological replicates; error bars depict the standard deviation of the replicates.

FIG. 3A shows the representative growth burves of *P. renovo* with and without addition of sodium nitrate to a final concentration of 4.5 mM at hour 54, following entry into the stationary growth phase. FIG. 3B shows *P. renovo* growth rate as a function of temperature. Average and standard deviation are from n=3 biological replicates. FIG. 3C shows a growth curve comparison of *P. renovo* at 8.75 and 35 g/L salinity. Average and standard deviation are from n=2 biological replicates. FIG. 3D shows endpoint biomass titer following 6 days of growth at varying salinities for *P. renovo*. Average and standard deviation from n=2 replicates are reported.

FIGS. 7a, 7b, 7c, and 7d depict an overview of *P. renovo* nuclear transformation. FIG. 7A shows a construct design showing genetic elements and primers used to generate DNA for electroporation (49 and 11) and subsequent PCR confirmation of transformants. FIG. 7B illustrates PCR verification of 12 clones utilizing primers shown in FIG. 7A. FIG. 7C shows fluorescent plate reader analysis of wild type and mCherry transformants, normalized to chlorophyll autofluorescence. An average and standard deviation of n+3 biological replicates are reported.

FIG. 7D shows confocal microscopy images of wild type and transformant microalgae expressing mCherry. Lighter coloring represents chlorophyll autofluorescence, red coloring represents mCherry fluorescence, 10 μm scale bar.

FIG. 8 depicts an overview of *P. renovo* chloroplast transformation.

DETAILED DESCRIPTION

Figure 1:
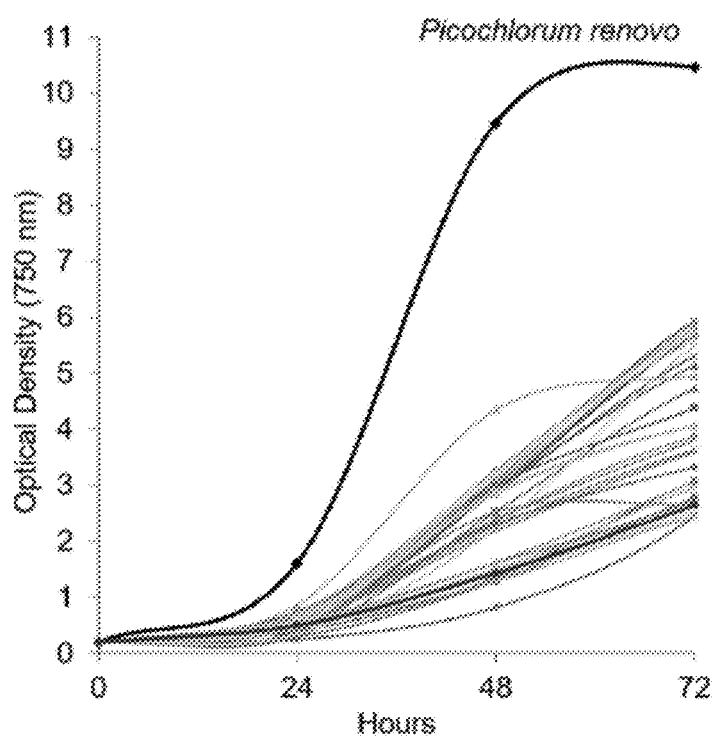
FIG. 1 depicts growth of over 100 halotolerant isolates under simulated growth conditions (diurnal light and temperature cycling) using a custom built photobioreactor. In an embodiment, *Picochlorum renovo* exhibited a noticeably faster growth rate and shorter lag phase relative to other isolates, including control strains *Nannochloropsis oceania* (KA32) and *Nannochloroplasis salina* (CCMP 1776).

Disclosed herein are a suite of genetic tools suitable for engineering both the nucleus and chloroplast in diverse microalgae. The efficacy of these tools were demonstrated as described herein on the algae *Picochlorum renovoi* and *Scenedesmus* sp. 46BD3, novel marine isolates down-selected from a culture collection. The tools described herein facilitate rapid chloroplast engineering, obtaining transgenic lines in as little as five days.

Microalgae are promising biocatalysts for applications in sustainable fuel, food, and chemical production. Described herein are culture collection screening, down-selection, and development of a high-productivity, halophilic, thermotolerant microalga, *Picochlorum renovo*. This microalga displays a rapid growth rate and high diel biomass productivity (34 g/m$^2$/day), with a composition well-suited for downstream processing. *P. renovo* exhibits broad salinity tolerance (growth at 107.5 g/L salinity) and thermotolerance (growth up to 40° C.), beneficial traits for outdoor cultivation. Disclosed herein is complete genome sequencing and analysis, and genetic tool development suitable for expression of transgenes inserted into either the nuclear or chloroplast genomes. Disclosed herein is an evaluation of mechanisms of halotolerance via comparative transcriptomic analyses, identifying novel genes differentially regulated in response to high salinity cultivation. The present disclosure may enable basic science inquiries into control mechanism governing *Picochlorum* biology and lay the foundation for development of a microalga with industrially relevant traits as a model photobiology platform.

Herein the characterization and development of a novel alga of the genus *Picochlorum, Picochlorum renovo* sp. nov. This alga was identified via screening of a greater than 300-strain algal culture collection, under simulated outdoor environmental conditions. Herein the diel biomass productivity (34 g/m$^2$/day) of this alga under simulated outdoor cultivation conditions, quantifying the protein, carbohydrate, and lipid content (20%, 60%, and 10% ash-free dry cell weight, respectively), thermotolerance (growth capacity up to 40° C.), and salinity tolerance (growth at 107.5 g/L salinity). Furthermore, nuclear, chloroplast, and mitochondrial genome sequences are reported herein, as are comparative transcriptomic analyses under low- and high-salt conditions, enabling high-resolution genome annotation and providing novel insight into the mechanisms of halotolerance. Also disclosed herein is a set of facile genetic tools that enable expression of multiple transgenes inserted into either the nuclear or chloroplast genomes. The present disclosure and the data provided herein may enable fundamental insights into *Picochlorum* photobiology and inform targeted genetic engineering strategies to accelerate microalgal biotechnological applications in a deployment-relevant, emerging model microalga.

Strain Down-Selection, Physiology, and Compositional Analysis

Figures 3A, 3B, 3C, 3D:
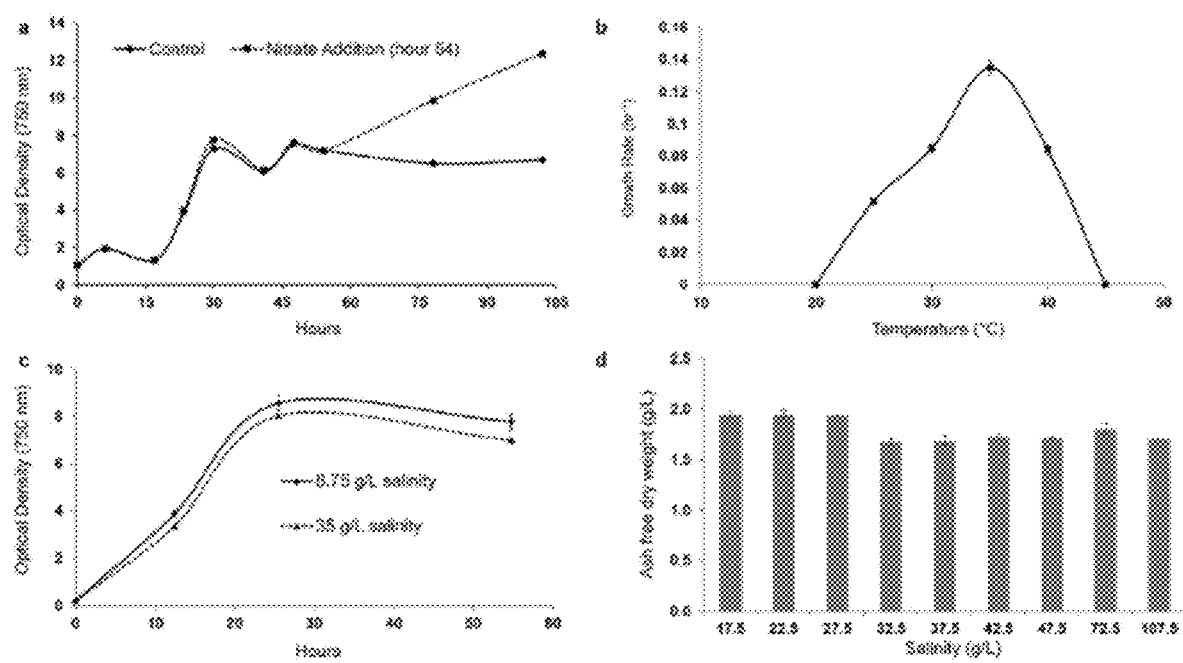
FIGS. 3a, 3b, 3c, and 3d depict the physiological characterization under varied nitrogen, temperature, and salinity regimes of *P. renovo*.

Over 100 unique halotolerant isolates were screened under simulated growth conditions (diurnal light and temperature cycling) using a custom built photobioreactor. One isolate exhibited a noticeably faster growth rate and shorter lag phase relative to other isolates, including control strains *Nannochloropsis oceania* (KA32) and *Nannochloroplasis salina* (CCMP 1776), two top-candidate strains currently under evaluation for outdoor deployment (FIG. 1). This rapidly growing strain was down-selected for further analysis and development. Under batch growth this microalga showed a diel biomass productivity of 34.3 g/m$^2$/day, from hour 6 to 30, representative of one day and night of high productivity growth (FIG. 2A). Dark period biomass loss was 0.25/g/m$^2$/hr during the first 11-hr dark period and 0.46 g/m$^2$/hr in the second. Cell division occurs during both light and dark periods when grown under a diel cycle. Cessation of cell division and biomass accumulation occurs simultaneously. Nitrogen supplementation during stationary phase led to growth re-initiation (FIG. 3A). Peak growth was observed at 35° C. under continuous illumination, with growth capacity up to 40° C. (FIG. 3B).

FIG. 1 shows representative culture collection growth screening data. The short lag, rapid growth, and high optical density phenotype of *P. renovo* is highlighted in black. *Nannochloropsis salina* CCMP 1776 is bolded in the figure for reference.

FIG. 2 shows an overview of *P. renovo* productivity and associated biomass composition as a function of time. Alternating shaded bars depict the light-dark growth cycle. FIG. 2A shows growth curves as a function of ash-free dry weight (AFDW) (g/L) and cell density (cells/mL). Areal productivity is shown for hour 6 to 30, representing one light-dark cycle (day). FIG. 2B shows the biomass content of liquid (as fatty acid methyl ester, FAME), carbohydrate, protein, and the fraction of biomass not identified. FIG. 2C shows carbohydrate speciation via hydrolysis of biomass. FIG. 2D shows fatty acid speciation via fatty acid methyl ester analysis, representative of the lipid fraction of the biomass. All data points are an average of n=3 biological replicates; error bars depict the standard deviation of the replicates.

FIG. 3 shows the physiological characterization under varied nitrogen, temperature, and salinity regimes of *P. renovo*. FIG. 3A shows the representative growth burves of *P. renovo* with and without addition of sodium nitrate to a final concentration of 4.5 mM at hour 54, following entry into the stationary growth phase. FIG. 3B shows *P. renovo* growth rate as a function of temperature. Average and standard deviation are from n=3 biological replicates. FIG. 3C shows a growth curve comparison of *P. renovo* at 8.75 and 35 g/L salinity. Average and standard deviation are from n=2 biological replicates. FIG. 3D shows endpoint biomass titer following 6 days of growth at varying salinities for *P. renovo*. Average and standard deviation from n=2 replicates are reported.

Biomass composition varies as a function of growth phase, with fluctuations in carbohydrate and protein content observed throughout diel cycles (FIG. 2B). Notably there is a substantial decrease in glucose (presumably from starch utilization) following inoculation into fresh media, with glucose declining from 52% to 1.4% of AFDW (FIG. 2C). Lipid content, as measured by FAME, varied from 8.5-16.2%, with C16:0, C16:3, C18:1n9, C18:2n6, and C18:3n3 representing major lipid fractions (FIG. 2D). 30 hours post-inoculation the cells center the stationary phase and have an ash-free composition of 10% FAME, 20% protein, 59.5% carbohydrates (measured as hydrolyzed monomeric sugars), and 10.5% unidentified biomass components (FIG. 2B).

Genomic Analysis and Speciation

Phylogenetic analysis of the isolate's 18S rRNA showed high similarity (>99%) to numerous *Picochlorum* species, providing an initial line of evidence for taxonomic classification. PacBio genome sequencing generated an assembled nuclear genome containing 29 contigs with 14.4 Mbps and 46.2% GC, in line with previously reported *Picochlorum* genomes. 8,902 protein coding sequences were putatively annotated, with an average of 2.2 exons/1.2 introns per genes. The nuclear genome contains the universally conserved meiosis associated genes, including four rad51 homoloags, dmc1, pol2A, rfc1, polD1, mre11, rad50, rad51, rad54, mus81, msh4, msh5, rpa1, rpa2, and rap3. Further evidence of potential meiosis is provided by the identification of oda2 and bug22, which are flagella assembly associated genes, implicated in gamete pairing prior to mating. Identified herein is also a putative chlorophyllide-a oxygenase, necessary for chlorophyll b production, and cell division was observed to occur by autosporulation FIG. 4), providing additional evidence for classification of this strain as a *Picochlorum*. When compared to other available *Picochlorum* genomes, the novel *Picochlorum* isolate displayed 87-94% whole genome sequence identity (Table 1). These data support that the isolate is a novel *Picochlorum* species, henceforth termed *Picochlorum renovo* sp. nov.

Figure 4:
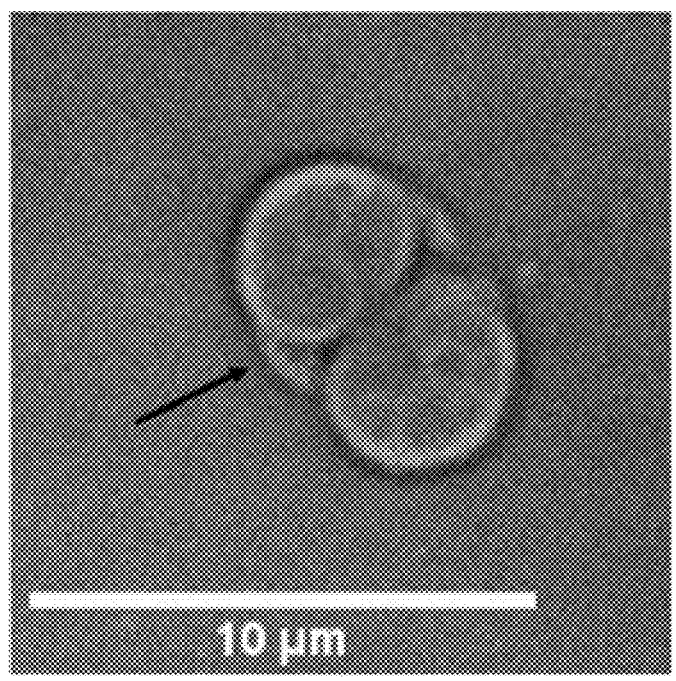
FIG. 4 depicts the division of *P. renovo* highlighting autosporulation and mother cell wall (indicated with an arrow), a defining trait of the *Picochlorum* genus. The highlighting indicates the chlorophyll autofluorescence.

FIG. 4 shows the division of *P. renovo* highlighting autosporulation and mother cell wall (indicated with an arrow), a defining trait of the *Picochlorum* genus. The highlighting indicates the chlorophyll autofluorescence.

TABLE 1

Whole genome alignment analysis of *Picochlorum* spp.

| Strain ID | Genome alignment (% identity) | Genome alignment (% query coverage) |
| --- | --- | --- |
| UTEX B2795 (*Picochlorum oklahomensis*) | 94 | 100 |
| SENEW3 (*Picochlorum* sp.) | 94 | 97 |
| RCC4332 (*Picochlorum costavermella*) | 87 | 62 |
| NBRC102739 (*Picochlorum* sp.) | 87 | 1.6 |
| DOE101 (*Picochlorum soloecismus*) | 88 | 0.7 |
| UTEX LB 1998 (*Picochlorum oculata*) | 88 | 0.6 |

Figures 5A, 5B:
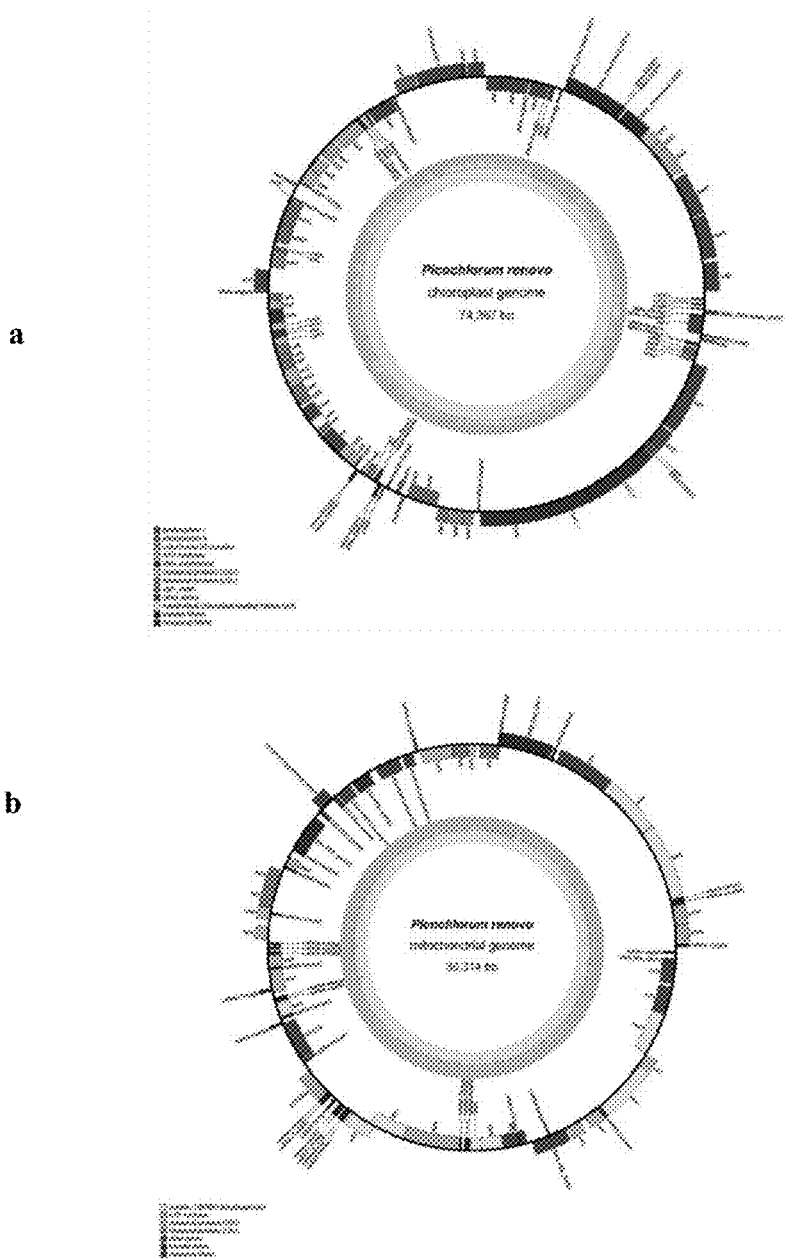
FIG. 5a depicts the chloroplast genome map of *P. renovo*.
FIG. 5b depicts the mitochondrial genome map of *P. renovo*.

Chloroplast and mitochondria genomes were separately assembled (FIG. 5). The 74 kb chloroplast genome displayed a non-canonical chloroplast genome architecture lacking an inverted repeat region, for the genus *Picochlorum*. The 36 kb mitochondrial genome displayed a compact coding architecture, representing the highest mitochondrial coding density reported to date (1.05 CDS/kb) for the class Trebouxiophyceae, in line with the previously reported mitochondrial genome of *Picochlorum costavermella*. Notably, genes encoding a homing endonuclease and protein of unknown function split the mitochondrial 23s rRNA, contributing, in part, to the higher coding density (FIG. 5). FIG. 5 depicts chloroplast and mitochondria genome maps of *P. renovo*.

Transcriptome Response to Salinity

Figure 6:
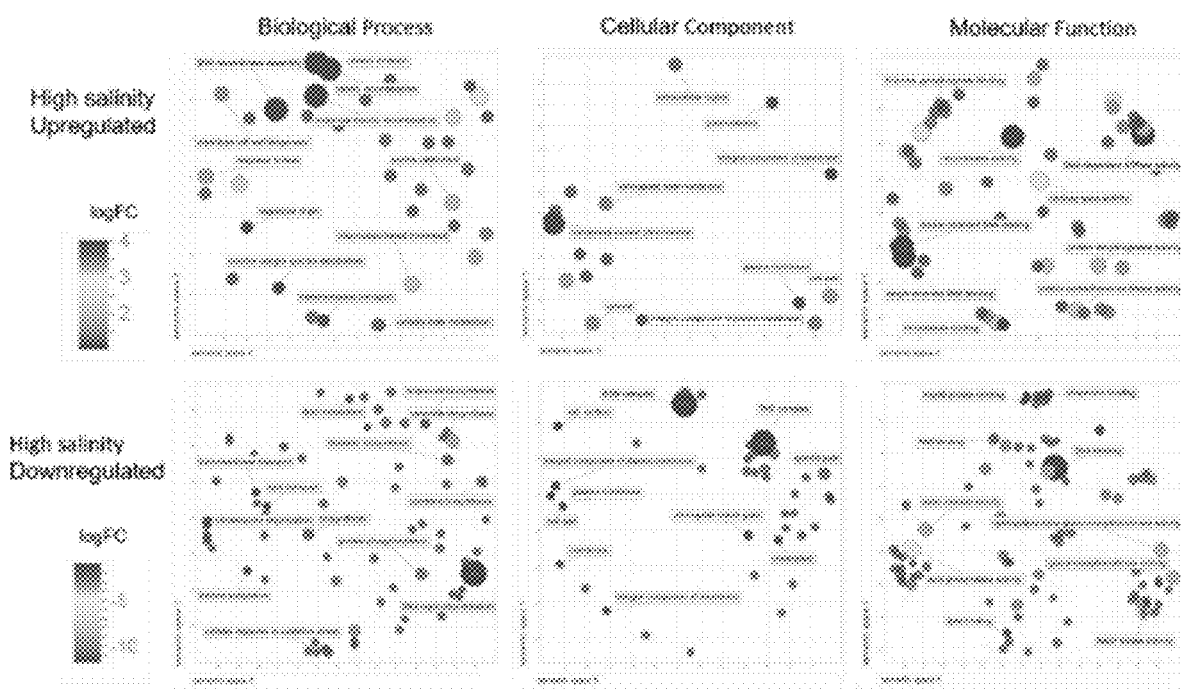
FIG. 6 depicts high salinity upregulation and high salinity downregulation of various differentially-expressed transcripts, implicating a subset of processes involved in the high-salt response.

A broad halotolerance in *P. renovo* was observed, with cultivation capacity in minimal media salinity concentrations ranging from 8.75-107.5 g/L sea salts (FIG. 3). To investigate the genes involved in the salinity response, cultures were grown in 8.75 and 35 g/L salinity seawater and assessed via comparative transcriptomics. RNA from triplicate mid-log phase cultures was sequenced, and subsequent differential expression analysis was performed. 3,464 genes were differentially-expressed at 35 g/L salinity (1934 down, 1530 up) at statistically significant values (q<0.05), representing 39 percent of total coding sequences (Table 2). Gene ontology semantic analyses were used to deconvolute the large number of differentially-expressed transcripts, implicating a subset of processes involved in the high-salt response, including previously reported genes governing proline metabolism (FIG. 6). A series of previously unreported haloresponsive genes were also observed, including ppsA and ppsC (phthiocerol synthesis polyketide synthases), pks1 and pks15 (phenolphthiocerol synthesis polyketide synthases), input1 (inositol phosphorylceramide glucuronosyltransferase), cerk (ceramide kinase), rad54 (DNA repair and recombination protein), and dmc1 (disrupted meiotic cDNA 1), discussed further below.

All differentially expressed genes from mid log phase *P. renovo* cultures grown at 8.75 and 35 g/L seawater salinity were tabulated and can be found in Appendix A (also referred to herein as Table 2) of the as-filed provisional application No. 62/884,918 filed on 9 Aug. 2019, the contents of which are hereby incorporated in their entirety.

Nuclear and Chloroplast Engineering

A linear PCR amplicon containing native promoter and terminator elements, directing transcription of 2A peptide-linked bleomycin resistance gene and the fluorescent reporter mcherry (FIG. 7A) was transformed into *P. renovo* via electroporation.

FIG. 7 illustrates an overview of *P. renovo* nuclear transformation. FIG. 7A shows a construct design showing genetic elements and primers used to generate DNA for electroporation (49 and 11) and subsequent PCR confirmation of transformants. FIG. 7B illustrates PCR verification of 12 clones utilizing primers shown in FIG. 7A. FIG. 7C shows fluorescent plate reader analysis of wild type and mCherry transformants, normalized to chlorophyll autofluorescence. An average and standard deviation of n+3 biological replicates are reported. FIG. 7D shows confocal microscopy images of wild type and transformant microalgae expressing mCherry. Lighter coloring represents chlorophyll autofluorescence, red coloring represents mCherry fluorescence, 10 μm scale bar.

Per transformation, an average of 41 colonies were obtained, representing transformation efficiencies of 14 colonies per g of DNA, and $9 \times 10^{-8}$ colonies per electroporated cell. 75% (9/12) of PCR screened transformants contained the entire transgene construct, while the remaining contained truncated versions (FIG. 7B). Positive transformants showed a 2-to-4-fold increase in mCherry fluorescence over wild type (FIG. 7C), and confocal microscopy confirmed mCherry fluorescence localized to the nucleus and cytoplasm in these cells (FIG. 7D). Additional promoter configurations, with and without their respective introns, were also evaluated, including elongation factor 1-alpha 2 and photosystem I reaction center subunit II (psaD), both utilizing the eef1A2 (elongation factor 1-alpha 2) terminator, which displayed comparable transformation efficiencies and mCherry fluorescence (Table 3). *P. renovo* is also sensitive to G418 and may be successfully used as a selection agent.

DNA elements: promoters, terminators, introns, selection markers, reporters, and primers utilized in this study as well as transformation efficiencies and mCherry fluorescence of alternative nuclear engineering constructs can be found in Appendix B (also referred to herein as Table 3) of the as-filed provisional application No. 62/884,918 filed on 9 Aug. 2019, the contents of which are hereby incorporated in their entirety.

TABLE 3

Rubisco small subunit promoter
(SEQ ID NO. 1)
TGGATTTCCTCAAGGATGAAGTGTCACAGCAATTTGAAAAAGTAGAAAA

AATTGCCAATGTGTTGGAGCAGATAGAGAAAAAACAAAAGACTCTGCGC

TATCGCCAGGATAAAGTGCAGTTTATGGCATCTAATATAAATGACAGAG

TGAAATTATTGGCAGAATGCATTGGGCGGTTCCTCAACCAGCATCTGAA

GCTGAGAAGCACTTCCAACACCATGAACTGCCCATGCTGGAGTCAAACA

CGGCATCATTAGCTCAAGAGGTAGCTATGCTCCGATCCCAGGCGCAAGC

AGTAAAACAATCAGGGAAAGTACAACAGTCACATGGCTCTGCTTCCAAA

GCCTCACCAAGTGATTTGCGAAGAATCAGGGAAATGCTATCAGAACACG

ACACCATCATTAGAGATATGTGCCGAAAGGTGCGAGCCATCGAGTCCAG

TGTATAGGGTTGTGTCTTCCTGCCGTGTCTGAAGAGGATGTAAAAAAAG

TGCCCTGATTTTTATATCGTAATTACGACCGAAGTTCCGTTTCCATGCA

TCGACGAAGCATGCTTCATTATCCTGATAAACACGTGAGGCATGCGCCT

CACCTGCACAATATAATTCAGTTTTTTTATCTTTGAAAACTTACTACAA

ACAAATTAACAAA elongation factor 1-alpha 2 promoter
(SEQ ID NO. 2)
TTATTTTAGAATGAATTCGATTGCTCTGAAGACATCGCTCGCTGGATGC

TCAAAGAGGGTATCCATCCCCATCGGCACCCACAGAACAGCACCAAGGC

TCTGTACTACTACTACTACAAGAACAAGGACCTGTCTTTACTCTGGTAA

CGGTAGCACCGGGGGTGATGATGTATCTACACCTGCAGTAGCAATTGCA

GTCGCAGGCCTTGCTTATCCGCCCATCGTCTTCTGGTCAGAGTACACCT

TGGCAACGACTGGAAGTGGCCTTCCTCCTGGCCCAGGTGGAGCATTGGG

TGCAGCAGAGGGTATTTCATACCTTGCAAGCGTGGGGATTGTCGCATGG

TCTCTCAAGACAAAGGTTCAGACTGGGAGTGGATTACCAGCGGGACCCA

GTGGTCTCGTGGGTGCAGCAGAGGGCGTTTCATACCTTGCAGTGCTTGG

TGGATTGATTGCCGCAGGCGTGTCCACCATGTCGTAAAGAAGAAAGTCG

GAATAGGATTCCAATTCCCGAATTAGTTTGACCACCATTGTGGGCGCAT

GTGCGGCTGACTCCCTCAAGTTCTCATGTCCACACCCGAAATAGCCCTC

TTAAAAACATATATTGTTAGTTATAAACTCAGTGTTGTTAACTATCTCT

AAAAACATTTAAA photosystem I reaction center subunit II promoter
(SEQ ID NO. 3)
GTGCAGAATACATACACAACCTTCGATGATGATGATGGAAGAAGGTGAT

AGTGTAGCATGGGAAGGGGAGACGTACGAGCCGGACAATGTCATTTGTG

GAGACGGGAGAACTGCGCCTGATGGTCACATGCTCAAGTTCATTCAACA

CATGGCAGCCATCCCTGATCAATGTCTGAGGCTCCTATACACGGCTCGC

GACAGGCTCGCTGCATTTAGAATCAAACAAAGAATTAATTGAAAATCAG

GCAACATTGTCCATCCTGCAATGCCCCACGAGCATGCGTTGCCCAAGTA

ACCTCCCCACTCATTGCAGCACTGATCGAGTCCTTGGATATGGTTCCAG

CAACAGACCACTTCCGGTCACCTCCCTCCTCCTGGGAATGGGCCATCAT

AGAAATACGGATATGTAGCAAACTTTGTACGCATGAAAATGATCGAGAC

AAGGCCATACCGATCGAAGAAGCTGTCAACACTATGGGAAGCTTGAAC

CTTTGCCTGGGTCAAAAGGATTCCACCTCGTCCCGAATTAGTTTGGACA

CAATCGCCTGGAACGTCCAAAAAGATAACAGCAAAATCTCCACATTCCT

CCTTATCGATTATCCTACTTTTACCCCTTTCCATCTTGGCTATTTCCTT

GGATTAATAGAAA elongation factor 1-alpha 2 terminator
(SEQ ID NO. 4)
GATGTTGACTGCTATGTGATGAGATGGCCGATCAAATTGTCAGTGGTGG

TGCTTTTGCATCAACATGGATTCTGGTTGGCTTGATCAATAATTATTTT

GCATAGTTTTTTACACAACATCTATTATTCTTGTAATATGGGTCAGAAA

GCCTTGGTTTACACAGATGCACTGCCATCACCATCATCATCATCATCAT

CAGTGGTGCAGTCAACAGATTCTTCTGGCAACGTTGGCCGACTGATTTC

ATCGATTCCCTTTTGAATTTATCAACCAATTGCTTCATATACGATGGTG

AACATCTGTTAACAAGCTCTTTTGGATACATCTGGCAAATGCTCATCAT

GGAATGATGCAATGCAGGATTCTTCTCCCCTGTATGTTTAGAATAGAAT

AGAATATGTAACAAGATGAAGCAACGGACAACAACTGGAAGCATAGTAT

GGAAATGTATGTACCTTGGGCTATGAGTG

Rubisco small subunit intron
(SEQ ID NO. 5)
GTATGATTTACATGTTTATTGAAGCACAGTTTATGACACGCGTGAGCTC

CAATGCGCGACTTTCCAAGTCAGCGCCTCGGTGCACTCCGCCAATGTGA

ACAAGGCGCTAACCCTCGTTGTTTGTCATTATGCAG elongation factor 1-alpha 2 intron
(SEQ ID NO. 6)
GTACGTTTTGGTGGCATCAGAGGCTGCGCACAGATCAGAGGCGGCCTTC

GTAACTGTCCTTGGACGCCTGTGGCGGTAGCATGCATGCATGATAATGT

TTTATAATTATGAATTTAATGCACATGGTATATATACTGACTGAATTCT

GTGTACCCATGCAG photosystem I reaction center subunit II intron
(SEQ ID NO. 7)
GTACGTAGGAAGTCTTATCAAGACTGTTGATGAAGCGGATGTCAACTCG

CTGGAATTCTGCGTCTTTGGGCCGATGGCTTCCATGTAGAGTAGTATTT

TGTTTATTATTTATATCATGATTTGATCGCGTATGGTTATGGGATATTA

TTGAGTGTGTGAGTGTCACCACCAGCGAGGATACGGCGAGTCTAGGATG

GGGCTCGGATTCTGTGGGCGATGGGACCCAACGAATCAGTGTTCCAGAC

TABLE 3-continued

```
AAGTGTATTCGTAGGGTTGGGGAATGAGAAGGCTACCAAATACATACGT
AGCTCAAGATACGGGTTATGAAACAAGGCATTGCTCTGACATGAATGTT
GTTGGTGTACAG
``` bleomycin resistance
(SEQ ID NO. 8)
```
ATGGCCAGGATGGCCAAGTTGACGTCAGCCGTTCCAGTTCTCACAGCCA
GGGACGTGGCCGGTGCTGTTGAGTTCTGGACAGATCGGCTTGGTTTCTC
CCGAGATTTCGTGGAAGATGACTTTGCAGGCGTAGTTAGAGATGACGTG
ACGCTGTTTATCTCTGCCGTGCAGGATCAGGACCAAGTGGTGCCCGACA
ATACACTGGCTTGGGTCTGGGTGCGTGGGCTGGATGAGTTATATGCCGA
GTGGAGCGAAGTTGTCTCCACTAATTTTCGTGATGCATCTGGTCCAGCA
ATGACGGAGATTGGAGAACAGCCATGGGGGCGCGAGTTTGCATTGAGAG
ATCCAGCGGGCAACTGTGTACATTTTGTTGCGGAGGAACAGGAT
```

2A
(SEQ ID NO. 9)
```
CTGTTGGCCATTCATCCAACTGAGGCTCGCCATAAGCAGAAAATTGTGG
CACCCGTCAAGCAGACTTTGAATTTCGATCTTCTTAAATTGGCTGGCGA
CGTGGAATCTAATCCAGGACCT
``` mCherry
(SEQ ID NO. 10)
```
ATGGTCAGTAAGGGAGAGGAAGACAATATGGCAATCATCAAGGAATTTA
TGAGATTCAAAGTGCATATGGAGGGTAGTGTAAACGGGCACGAATTTGA
AATTGAGGGCGAGGGGGAAGGTAGACCTTACGAGGGGACACAGACAGCT
AAACTTAAGGTCACTAAGGGCGGTCCTCTACCATTTGCCTGGGACATTC
TTTCGCCGCAATTCATGTATGGCAGCAAGGCTTATGTTAAACATCCTGC
CGATATCCCAGATTACCTCAAGCTTTCTTTCCCAGAGGGATTCAAGTGG
GAGCGAGTGATGAATTTTGAAGACGGCGGTGTTGTCACTGTGACGCAGG
ACTCTTCCTTGCAGGACGGAGAATTCATCTATAAAGTGAAGCTCAGAGG
CACAAATTTTCCTTCAGATGGTCCTGTGATGCAGAAAAAAACAATGGGG
TGGGAGGCGTCCTCAGAGAGGATGTATCCAGAGGATGGAGCACTCAAGG
GGGAAATTAAACAGAGATTAAAGCTGAAAGACGGAGGCCATTATGATGC
TGAAGTGAAAACTACCTACAAAGCGAAAAAGCCTGTGCAGCTTCCTGGA
GCATATAATGTGAACATAAAATTGGATATTACTTCGCACAATGAGGATT
ATACTATTGTCGAACAGTATGAACGGGCAGAAGGAAGACACTCTACGGG
CGGCATGGATGAGCTTTACAAATAA
```

G418 (Geneticin) resistance
(SEQ ID NO. 11)
```
ATGATCGAGCAAGACGGTCTTCATGCGGGGAGTCCTGCGGCCTGGGTGG
AGCGACTTTTTGGTTACGATTGGGCTCAGCAAACAATAGGATGTTCAGA
CGCAGCAGTTTTTCGGCTCTCGGCCCAGGGTAGGCCTGTACTTTTCGTG
AAAACAGATTTGAGCGGTGCTCTGAACGAACTTCAAGATGAAGCCGCTC
GCCTCAGCTGGTTAGCAACAACGGGGGTCCCGTGCGCCGCTGTGTTGGA
CGTGGTGACCGAGGCGGGTAGGGATTGGTTGTTACTGGGAGAGGTGCCC
GGACAGGATTTACTTAGCTCGCATCTCGCACCAGCAGAGAAGGTAAGTA
TTATGGCAGACGCTATGAGACGTTTGCATACGTTGGATCCTGCAACATG
CCCGTTCGATCACCAAGCCAAACATCGAATTGAACGTGCACGAACAAGA
ATGGAGGCAGGGCTTGTTGACCAAGACGACTTAGATGAGGAACACCAGG
GTTTGGCCCCCGCAGAGTTATTTGCAAGGTTGAAAGCATCCATGCCCGA
TGGGGAAGATCTAGTCGTGACGCATGGGGACGCTTGTTTGCCTAATATA
ATGGTAGAAAATGGACGGTTCTCCGGTTTCATAGATTGTGGGCGTTTAG
GTGTGGCGGATCGTTATCAAGATATAGCCCTTGCCACAAGGGATATCGC
AGAGGAACTGGGAGGAGAATGGGCAGATAGATTTTTGGTTCTCTATGGG
ATTGCGGCACCAGATTCACAGCGAATTGCATTTTACAGGTTACTGGACG
AGTTTTTTTAA
```

Rubisco intron was placed after the 127th base pair of the bleomycin resistance gene
(...TTGCAG (HERE) GCGTAG...)

photosystem I reaction center subunit II intron was placed after the 204th base pair of the bleomycin resistance gene
(...ACACTG (HERE) GCTTGG...)

elongation factor intron was placed after 259th bases pair of the bleomycin reistance gene
(...AAGTTG (HERE) TCTCCA....)

Chloroplast Vector:
Upstream homology region
(SEQ ID NO. 12)
```
GCGAGGGTAGCAAATGGGATTAGATACCCCAGTAGTCCTCGCCGTAAAC
GATGGATACTAGGTGTTGGATGGGTTCAAATCATTCAGTACCGTAGCTA
ACGCGTGAAGTATCCCGCCTGGGGAGTATGCTCGCAAGAGTGAAACTCA
AAGGAATTGACGGGGGCCCGCACAAGCGGTGGAGCATGTGGTTTAATTC
GATGCAACGCGAAGAACCTTACCAGGGCTTGACATGTCACTTTTTTCTT
GAAAGAGAAAGTTCCCGAGTGAACACAGGTGGTGCATGGCTGTCGTCAG
CTCGTGTCTTGAGATGTTGGGTTAAGTCCCGCAACGAGCGCAACCCTTA
TTCTGTGTTGCTATTTGATAGGAAACTCAGAAGACTGCCGGTGATAAGC
CGGAGGAAGGTGAGGATGACGTCAAGTCAGCATGCCCCTTACGCCCTGG
GCTACACACGTGCTACAATGGCCGGGACAAAGAGATGCAATCTCGCGAG
AGCAAGCTAACCTCAAAAACCCGGTCTTAGTTCGGATTGTAGGCTGAAA
CTCGCCTACATGAAGCTGGAATCGCTAGTAATCGCAGGTCAGCCATACT
GCGGTGAATACGTTCCCGGGCCTTGTACACACCGCCCGTCACACCATGG
AAGCTGGCTATGCCCAAAGTCGTTACCCCAACCTTTTGGAGGGGGACGC
CTAAGGCAGAGCTAGTGACTAGGGTGAAGTCGTAACAAGGTAGCCGTAC
TGGAAGGTGCGGCTGGATCACCTCCTTAAAAAGGAAAATAAATAAAAAT
ACAATTTTGTATTTAAAAGTTCATATCATCTGTTATCCCTAAAAATCTA
GGGATACAGGCCGATGTACGGCCTGGGCTAATAGCCCACTTTTTCGATT
TTTTGAAAACAAATGGGCTATTAGCTCAGTTGGTTAGAGCGCACGCCT
GATAAGCGTGAGGTCACTGGTTCAACTCCAGTATAGCCCACCAGATAGA
TATTTATCTATAAAGAATTG
```

TABLE 3-continued

Downstream homology region
(SEQ ID NO. 13)
TTAAAAAGTGGGTGAACTTCATGATATTTTTATCATGGGGGTATAGCTC
AGTTGGTAGAGCGCTGCCCTTGCAAGGCAGAAGTCAGCGGTTCGAATCC
GCTTATCTCCACCATGTTTTTCTATTGAAAATATGGTAAAGAATTGGTC
AAATGACTTAAAGCATAGGGTGGATACCTAGGCACCTAAAGACGATGAA
GGGCGTGGAACCGACGATACGCTTCGGGGAGCTGGAAACGAGCTTTGAT
CCGAAGATTCCCGAATGGGGCAACCCAATAAACTATCCACTGAATTCAT
AGGTGGAAAAGAGATAACTTAGTGAACTGAAACATCTTAGTAGCTAAAG
GAAGAGAAAGCAAACGCGATTCCCGGAGTAGTGGCGAGCGAAATGGGAA
CAGCCTAAACCAATATTTTATATTGGGGTCGTGGGAAAACATGATTTAC
TAAGTTAAAAACAATTTAAATGAAACAGCTGAATCCTGTACCAAAGAAG
GTAAAAGTCCTGTAATTGAAAAATTTAATTTTAACTTTTAACAACTATG
TTAGTTATGTTTATCCCGAGTAGCATGGGACACGTGAAATCCCGTGTGA
ATCAGCGAGGACCACCTCGTAAGGCTAAATACTCTTAGGTGACCGATAG
TGAAGTAGTACCGTGAGGGAAAGGTGAAAAGAACCCCTGTAGGGGAGTG
AAATAGAACATGAAACCCTATGCTGACAAACAGTGGGAGGTACTTCAAG
TACTGACCGCGTACCTGTTGAAGAATGGGCCGGCGACTTAGAAAGAGTG
GCAAGGTTAAAGACAATAATCTGGAGCCAGAGCGAAAGCAAGTCTGAAT
AGGGCGAGTTAAGTCACTTTTTCTAGACCCGAACCCGGGTGATCTAACC
ATGACCAGGATGAAGCTTGGGTAACACCACGTGAAGGTCCGAACCGACT
GATGTTGAAAAATCAGCGGATGAGTTGTGGTTAGCGGTGAAATACCAGT
CGAACTCGGAGCTAGCTGGT 16S Promoter
(SEQ ID NO. 14)
TAGTCATATATTAATTTTTACTACATATATATATTGGTTTGTTAAAAAATT
TATATTTTCCAGTTAGATTCTGGAAAATATGATATAAAGAGAGGCAGAG
TGGTTTGACTTTTTATCAGAACATGATACATTAATCAATGTGAAAAAAT
TTC Ribosomal Binding Site
(SEQ ID NO. 15)
AGGAGGTTATAAAAA superfolder GFP (sfGFP)
(SEQ ID NO. 16)
ATGAGCAAAGGAGAAGAACTTTTCACTGGAGTTGTCCCAATTCTTGTTG
AATTAGATGGTGATGTTAATGGGCACAAATTTTCTGTCCGTGGAGAGGG
TGAAGGTGATGCTACAAACGGAAAACTCACCCTTAAATTTATTTGCACT
ACTGGAAAACTACCTGTTCCATGGCCAACACTTGTCACTACTCTGACCT
ATGGTGTTCAATGCTTTTCCCGTTATCCGGATCACATGAAACGGCATGA
CTTTTTCAAGAGTGCCATGCCCGAAGGTTATGTACAGGAACGCACTATA
TCTTTCAAAGATGACGGGACCTACAAGACGCGTGCTGAAGTCAAGTTTG
AAGGTGATACCCTTGTTAATCGTATCGAGTTAAAAGGTATTGATTTTAA
AGAAGATGGAAACATTCTCGGACACAAACTCGAGTACAACTTTAACTCA
CACAATGTATACATCACGGCAGACAAACAAAAGAATGGAATCAAAGCTA ACTTCAAAATTCGCCACAACGTTGAAGATGGTTCCGTTCAACTAGCAGA
CCATTATCAACAAAATACTCCAATTGGCGATGGCCCTGTCCTTTTACCA
GACAACCATTACCTGTCGACACAATCTGTCCTTTCGAAAGATCCCAACG
AAAAGCGTGACCACATGGTCCTTCTTGAGTTTGTAACTGCTGCTGGGAT
TACACATGGCATGGATGAGCTCTACAAATAA erythromycin resistance (ereB)
(SEQ ID NO. 17)
ATGAGGTTCGAAGAATGGGTCAAAGATAAGCATATTCCTTTCAAACTGA
ATCACCCTGATGATAATTACGATGATTTTAAGCCATTAAGAAAAATAAT
TGGAGATACCCGAGTTGTAGCATTAGGTGAAAATTCTCATTTCATAAAA
GAATTTTTTTGTTACGACATACGCTTTTGCGTTTTTTTATCGAAGACC
TCGGTTTTACTACGTTTGCTTTTGAATTTGGTTTTGCTGAGGGTCAAAT
CATCAATAACTGGATACATGGACAAGGAACTGACGATGAAATAGGCAGA
TTCTTAAAACACTTCTATTATCCAGAAGAGCTCAAAACCACATTTCTAT
GGCTAAGGGAGTACAATAAAGCAGCAAAAGAAAAAATCACATTTCTTGG
CATTGATATACCCAGAAATGGAGGTTCATACTTACCAAATATGGAGATA
GTGCATGACTTTTTTAGAACAGCGGATAAAGAAGCACTACACATTATCG
ATGATGCATTTAATATTGCAAAAAAGATTGATTACTTCTCCACATCACA
GGCAGCCTTAAATTTACATGAGCTAACAGATTCTGAGAAATGCCGTTTA
ACTAGCCAATTAGCACGAGTAAAAGTTCGCCTTGAAGCTATGGCTCAA
TTCACATTGAAAAATATGGGATTGATAAATATGAGACAATTCTGCATTA
TGCCAACGGTATGATATACTTGGACTATAACATTCAAGCTATGTCGGGC
TTTATTTCAGGAGGCGGAATGCAGGGCGATATGGGTGCAAAAGACAAAT
ACATGGCAGATTCTGTGCTGTGGCATTTAAAAAAACCCACAAAGTGAGCA
GAAAGTGATAGTAGTAGCACATAATGCACATATTCAAAAAACACCCATT
CTGTATGATGGATTTCTAAGTTGCCTACCAATGGGCCAAAGACTTAAAA
ATGCCATTGGTGATGATTATATGTCTTTAGGTATTACTTCTTATAGTGG
GCATACTGCAGCCCTCTATCCGGAAGTTGATACAAAATATGGTTTTCGA
GTTGATAACTTCCAACTGCAGGAACCAAATGAAGGTTCTGTCGAGAAAG
CTATTTCTGGTTGTGGAGTTACTAATTCTTTTGTCTTTTTTAGAAATAT
TCCTGAAGATTTACAATCCATCCCGAACATGATTCGATTTGATTCTATT
TACATGAAAGCAGAACTTGAGAAAGCATTCGATGGAATATTTCAAATTG
AAAAGTCATCTGTATCTGAGGTCGTTTATGAATAA 16S Terminator
(SEQ ID NO. 18)
AAAAGGAAAATAAATAAAAATACAATTTTGTATTTAAAAGTTCATATC
ATCTGTTATCCCTAAAAATCTAGGGATACAGGCCGATGTACGGCCTGGG
CTAATAGCCCACTTTTTCGATTTTTTGAAAAACAAAT Primers:
oLRD011
(SEQ ID NO. 19)
CACTCATAGCCCAAGGTACATACATTTCCATAC oLRD049
(SEQ ID NO. 20)
TGGATTTCCTCAAGGATGAAGTGTCACAG TABLE 3-continued

| | |
|---|---|
| oLRD057<br>ATGGCCAGGATGGCCAAGTTG | (SEQ ID NO. 21) |
| oLRD059<br>TTATTTGTAAAGCTCATCCATGCCGCC | (SEQ ID NO. 22) |
| oLRD069<br>/5Phos/ATCCTGTTCCTCCGCAACAAAATGTAC | (SEQ ID NO. 23) |
| oLRD073<br>ACCAAGGCTTTCTGACCCATATTACAAG | (SEQ ID NO. 24) |
| oLRD078<br>TTTATATCGTAATTACGACCGAAGTTCCGTTTCC | (SEQ ID NO. 25) |
| oLRD205<br>TGGGCCGTAACTGACACTGAGAGAC | (SEQ ID NO. 26) |
| oLRD206<br>CAACTCCAGTGAAAAGTTCTTCTCCTTTGCTCAT | (SEQ ID NO. 27) |
| oLRD216<br>CCAACTGCAGGAACCAAATGAAGGTTCTGTC | (SEQ ID NO. 28) |
| oLRD217<br>GTGCTTTACCCCTAGATAGCCTTGCTGAC | (SEQ ID NO. 29) |

Table 4 depicts constructs tested, transformant colonies per transformation and range of increase of transformants in mCherry fluoresce over control.

TABLE 4

| Additional constructs tested | Transformant Colonies per transformation | Range of increase of transformants in mCherry flouresce over control |
|---|---|---|
| Elongation Factor 1-alpha 2 Promoter, without intron | 70 | 2.0-2.5 |
| Elongation Factor 1-alpha 2 Promoter, with intron | 38 | 1.4-2.0 |
| Rubisco small subunit promoter, without intron | 34 | 1.6-2.6 |
| Rubisco small subunit promoter, with intron | 23 | 2.0-2.5 |
| photosystem I reaction center subunit II promoter without intron | 9 | 1.5-2.2 |
| photosystem I reaction center subunit II promoter with intron | 7 | 1.8-2.0 |

Figures 8A, 8B, 8C, 8D:
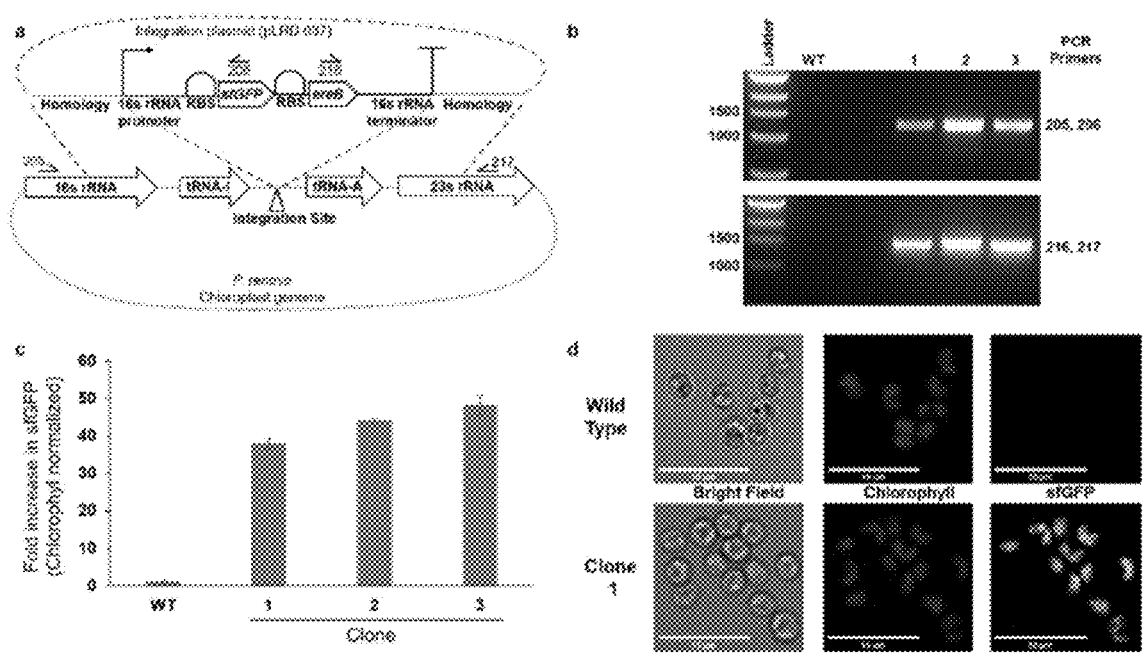
FIG. 8A is a construct design showing genetic elements utilized and homology directed integration into the chloroplast genome, along with the primers used for subsequent PCR confirmation of transformants.
FIG. 8B shows PCR verification of 3 clones utilizing primers shown in FIG. 8A.
FIG. 8C shows fluorescent plate reader analysis of wild type and sfGRP transformants, normalized to chlorophyll autofluorescence. Average and standard deviation of n=3 biological replicates are reported.
FIG. 8D shows eiplouroescent microscopy images of wild type and sfGFP transformant microalgae. Dark coloring represents chlorophyll autofluorescence, lighter coloring represents sfGFP fluorescence, 10 μm scale bar.

FIG. 8A depicts the construct utilized for targeted engineering of the *P. renovo* chloroplast via biolistics. The native 16s ribosomal RNA promoter and terminator were utilized to direct transgene expression. The commonly utilized antibiotics spectinomycin and streptomycin failed to inhibit *P. renovo* growth, and the above utilized phleomycin (for nuclear transformation) was ineffective for isolation of viable chloroplast transformants. Therefore, we chose erythromycin for selection, following antibiotic sensitivity screening. Notably, there is 100% homology between the last 9 base pairs (anti-Shine-Dalgarno sequence) of the *P. renovo* 16S rRNA and the *E. coli* 16S rRNA. Thus, a canonical *E. coli* ribosomal binding site (RBS, AGGAGGT-TATAAAAA) was used to direct translation. The erythromycin resistance gene (ereB) was linked to the reporter super folder green fluorescent protein (sfGFP) in an operon for rapid identification of transgenic lines. When fully constructed, this plasmid readily yielded transformed microalgae using a conventional biolistic approach.

FIG. 8 shows an overview of *P. renovo* chloroplast transformation. FIG. 8A is a construct design showing genetic elements utilized and homology directed integration into the chloroplast genome, along with the primers used for subsequent PCR confirmation of transformants. FIG. 8B shows PCR verification of 3 clones utilizing primers shown in FIG. 8A. FIG. 8C shows fluorescent plate reader analysis of wild type and sfGRP transformants, normalized to chlorophyll autofluorescence. Average and standard deviation of n=3 biological replicates are reported. FIG. 8D shows eiplouroescent microscopy images of wild type and sfGFP transformant microalgae. Dark coloring represents chlorophyll autofluorescence, lighter coloring represents sfGFP fluorescence, 10 μm scale bar.

Transformants could be rapidly identified via reporter gene by imaging of the bombarded plate in a gel imaging station with filter sets suitable for sfGFP detection. This procedure yielded an average (n=3) of a single colony per transformation with efficiencies of 1.4 colonies per g delivered DNA and $8 \times 10^{-9}$ colonies per microalgal cell. Colonies positive for sfGFP were passaged on selective media and proper integration of the construct into the target region was verified via PCT using primers binding outside the homology region and within the transgene operon, depicted in FIG. 8A and FIG. 8B. 38-48-fold greater sfGFP fluorescence was observed over wild type when measured via fluorometry (FIG. 7C). Epifluorescent microscopy showed sfGFP fluorescence successfully localized to the chloroplast (FIG. 8D).

DISCUSSION

*P. renovo* displayed a distant phenotype, including rapid growth rate and short lag phase in initial screening trials comparing over 100 unique isolates (FIG. 1). Peak growth rate at 35° C. (FIG. 3D) indicates this strain is well-suited for outdoor cultivation in high temperature regions with saltwater access. The diel biomass productivity reported here exceeds the target productivity of 25 g/m²/day for cost-competitive algal biofuels. Higher biomass productivities are likely achievable, given the suboptimal growth temperatures used in the tests described herein, which simulated outdoor cultivation in Mesa, Ariz. Future studies will evaluate outdoor productivity metrics to assess translatability of indoor metrics to outdoor systems in geographic regions better suited for high temperature cultivation.

Biomass analysis indicates the primary storage molecule in *P. renovo* is glucose, presumably in the form of starch, which is a favorable feedstock for downstream biotechnical applications. A drastic depletion of glucose was observed following inoculation into fresh media, similar to outdoor cultivation trends observed in other microalgal genera (FIG. 2C). Dark period biomass loss is characterized almost exclusively by a decrease in glucose. These phenomena putatively function as a mechanism to remobilize glucose as an energy source for cell division and cellular homeostasis. Thus, dark period biomass loss is an important parameter to consider when cultivating microalgae for biomass production. In the tests described herein, dark period biomass loss ranged from 0.25 to 0.46 g/m²/hr. Combined, these data highlight the potential advantage of harvesting *P. renovo* biomass prior to dark period losses to maximize biomass and storage carbon yields.

Cell division occurs during both the light and dark periods when grown under a diel cycle (FIG. 2A). This is contrary to many microalgae that synchronize cell division to occur at night; such is the case for the genera *Chlamydomonas, Nannochloropsis, Chlorella,* and *Scenedesmus*. This continuous diurnal and nocturnal cell division, coupled with the compact genome(s), may partially explain the rapid doubling time and high biomass productivity of *P. renovo*. Cell division and biomass accumulation cease concurrently, suggesting a non-photosynthetic state when nitrogen-deprived (FIG. 2A). This is notable as some microalgae will continue to accumulate biomass post-nitrogen deprivation, presenting another avenue for comparative analyses. Importantly, addition of nitrogen following growth arrest resulted in reinitiated growth, implicating nitrogen deprivation as a key driver for entry into stationary phase under the conditions evaluated in this study (FIG. 3A). Optimization of nitrogen levels and harvest point may lead to enhanced productivity and storage carbon content.

Comparative transcriptomic analyses identified a series of previously unreported, haloresponsive genes, dmc1, which is involved in homogous chromosome pairing during meiosis was one of the most highly upregulated transcripts at higher salinity. rad54, encoding a putative DMC1-interacting protein known to function during homologous recombination, is concurrently upregulated. The upregulation of these genes could be attributed to meiosis, or homologous recombination repair of double strand DNA breaks, due to increased double strand breaks at higher salinities. The observation of differentially-expressed genes associated with meiosis and homologous recombination suggests *P. renovo* may participate in sexual mating, and is capable of DNA repair via nuclear homologous recombination, both powerful tools for genetic manipulation. Further, the putative linkage to meiosis, homologous recombination, and saline responsiveness provides a potential mechanism to control these processes in *P. renovo*.

Downregulation of genes encoding proteins relating to lipid remodeling was observed under high salt conditions, including pks1, pks15, ppsA, ppsC, iput1, and cerk. ppsA and ppsC are involved in the synthesis of phthiocerol, while pks1 and psk15 are involved in the synthesis of phenolphthiocerol. Phthiocerol and its derivatives have been implicated in cell wall permeability. cerk is an enzyme that transfers a phosphate group to ceramide and it potentially acting in coordination with iput which transfer a glucuronic acid moiety to glycosyl inositol phosphorylceramides. Ceramides provide the lipid backbone for plant sphingolipids, and are primarily believed to be structural components of cellular membranes; however, ceramides have also been suggested to play a role in plant signaling. The above data suggests that *P. renovo* is potentially using lipid remodeling to tune membrane permeability at differing salinities.

To facilitate *P. renovo* genetic and metabolic engineering, the present disclosure provides tools enabling transgene expression in both the nucleus and chloroplast. Only 9 of the 12 nuclear transgenic isolates screened showed insertion of the full transgene construct. Of the remaining 3 isolates, 2 were shown to have a truncated promoter or terminator, and one was shown to have an incomplete mCherry coding sequence, observed by the inability to generate a full-length coding sequence PCR product (FIG. 7B). It is not clear whether these truncated transgene constructs are the result of native *P. renovo* machinery cleaving the transgene construct or an incomplete PCR product integrating into the genome. Fluorescent plate reader analysis of the clones revealed increased in mCherry fluorescence over wild type for the 11 clones containing a fully length mCherry coding sequence (FIG. 7B and FIG. 7C). A single clone without a full length mCherry lone without a full length mCherry coding sequence did not show an increase in mCherry fluorescence relative to wild type. The variation in mCherry fluorescence could be due to unique integration sites, or multiple integration events. mCherry fluorescence could be due to unique integration sites, or multiple integration events. mCherry fluorescence was primarily localized to the nucleus and cytoplasm of the transformant, with no observable chloroplast localization.

Successful chloroplast transformation was phenotypically observed via high reporter expression, and epifluorescent microscopy confirmed successful localization of the sfGFP to the *P. renovo* chloroplast, evident by overlap with chlorophyll autofluorescence (FIG. 8C and FIG. 8D). The ability to confirm transgenic colonies via direct imaging the high sfGFP signal will increase the throughput of control element screening, such as varied promoter strengths, in order to optimize metabolic engineering strategies. The successful utilization of an *E. coli* RBS for operonic expression presents the potential for optimization of mRNA translation via the employ of established RBS prediction software. Thus, these tools will be useful for biotechnical applications, such as overexpression of desired industrial enzymes, or fine-tuned regulation of native and/or synthetic metabolic pathways for bioproduct formation.

The transformation procedure described herein is a facile protocol with relatively rapid turnaround time that may be completed in a few hours. Given the fast growth of this alga, transformant colonies may be generated in approximately 5 days, considerably faster than top-candidate deployment strains such as *Nannochloropsis*, wherein colonies need ~21 days of growth before verification analyses may be performed. Also provided herein are the sequence of two additional nuclear promoters (elongation factor 1-alpha 2 and photosystem I reaction center subunit II in Table 3), which have been utilized herein to generate transformants. These additional promoters could prove useful for expression of multiple transgenes from one nuclear targeting cassette.

CONCLUSION

The full biotechnical potential of microalgae has yet to be brought to bear at commercial scale, in part due to the lack of robust, high-productivity strains suitable for outdoor deployment. Further, algal genetics in non-model systems has proven to be a limiting factor in strain development and fundamental mechanistic probing of top-candidate deployment strains. Here, we characterize a novel halophilic, thermotolerant microalga that possesses a series of unique traits suitable for deployment and report the development of genomic and genetic tools. These tools will enable both fundamental and applied efforts in an emerging model system, including elucidation of key regulatory mechanisms governing rapid growth and halotolerance in microalgae, as well as strain engineering strategies targeting enhanced productivity and carbon partitioning.

Online Methods

Microalgae were screened under conditions representative of summer cultivation. Briefly, microalgae were screened by sparging 100 mL cultures with 2% $CO_2$ at 100 mL/min. Temperature cycled from 21 to 32° C. while lighting cycled from 0 to 965 μmol m$^{-2}$ s$^{-1}$ (the maximum output of the utilized lights). This temperature and lighting regime were designed to simulate the conditions measured in outdoor raceway ponds located at the Arizona Center for Algae Technology and Innovation testbed site located in Mesa, Ariz., during the time frame from Jun. 12 to Jul. 21, 2014. Culturing utilized a modified f/2 medium, termed NREL Minimal Medium (NM2), in seawater (Gulf of Maine, Bigelow Laboratory). The following were added to the indicated final concentrations following by addition of 12 M HCl to attain pH 8.0: NH$_4$Cl (5.0×10$^{-3}$ M), NaH$_2$PO$_4$.H$_2$O (0.313×10$^{-3}$ M), Na$_2$SiO$_3$.9H$_2$O (1.06×10$^{-4}$ M), FeCl$_3$.6H$_2$O (1.17×10$^{-5}$ M), Na$_2$EDTA.2H$_2$O (1.17×10$^{-5}$ M), CuSO$_4$.5H$_2$O (3.93×10$^{-8}$ M), Na$_2$MoO$_4$.2H$_2$O (2.60×10$^{-8}$ M), ZnSO$_4$.7H$_2$O (7.65×10$^{-8}$M), CoCl$_2$.6H$_2$O (4.20×10$^{-8}$ M), MnCl$_2$.4H$_2$O (9.10×10$^{-7}$ M), thiamine HCl (2.96×10$^{-7}$ M), biotin (2.05×10$^{-9}$M), cyanocobalamin (3.69×10$^{-10}$ M), and Tris base (24.76×10$^{-3}$ M). For genetic engineering, the concentration of seawater was diluted 4-fold with Milli-Q water (Millipore Corporation), ammonium bicarbonate was utilized in the place of ammonium chloride, and 1.5× vitamins (thiamine HCl, biotin, cyanocobalamin) were utilized. Agar (Bacto) plates were prepared by autoclaving 3% agar in Milli-Q water, followed by addition of an equal volume of sterile filtered NM2 (seawater diluted 2-fold) with 2× nutrients, trace metals, vitamins, and Tris buffer. Sterile filtered selection antibiotic was added as necessary to appropriate concentrations, defined below.

To obtain a more detailed analysis of P. renovo growth, the above conditions were utilized with a 120 mL culture volume. Mid-log phase seed culture was generated under the above diel conditions, as used to inoculate 36, 120 mL cultures at a starting optical density of 1.0, in biological triplicate. Inoculation occurred approximately halfway through the lighting cycle, as indicated in FIG. 2. Sterile water was added prior to samplings to account for evaporative loses. Cell counts were performed using an Improved Neubauer hemocytometer. To convert volumetric productivities to areal values, the cross-sectional area of the culture tubes (0.00459 μm$^2$) was employed.

Growth at varying salinites for FIG. 3D were done in the same fashion as culture collection screening except salt levels were varied by addition of sea salts (Sigma 59883). 17.5 g/L salinity was achieved via addition of seawater to milli-Q water and higher salinities utilized addition of sea salts. 100 mL of culture was harvested after 6 days of growth, utilizing the temperature and light cycling from the culture collection screening methods described above. Temperature optima data, represented in FIG. 3B, was generated by growing strains in NM2, with culture conditions of constant 400 μmol ma s$^2$ lighting, 2% constant CO$_2$ sparging, and 100 mL volume. To determine growth rates, optical density (750 nm) measurements were taken daily in FIG. 3B.

Ash-Free Dry Weight, Fatty-Acid-Methyl-Ester, Protein, and Carbohydrate Analysis Compositional analysis was carried out traditionally, with the following modification: a Carbopac PA1 HPLC column was utilized for sugar monomer (carbohydrate) analysis. Protein was quantified via CHN (carbon, hydrogen, and nitrogen) analysis, utilizing an Elementar VarioEL cube CHN analyzer according to the manufacture's specifications. Briefly, a 5 mg sample is combusted at 950° C., and subsequent gasses are carried via helium to reduction and adsorption tubes utilizing an intake pressure of 1200 psi and ultimately detected with a thermal conductivity detector. A nitrogen-to-protein conversion factor of 4.78 was used.

Genome Sequencing, Assembly, and Annotation

High molecular weight algal genomic DNA was extracted from cells imbedded in agarose, purified and concentrated using AMPure PB beads. The DNA was then fragmented using Covaris g-Tubes. Fragmented and purified DNA was processed for 20 kb SMRT bell library prep. The long insert libraries were size selected using a Blue Pippin instrument (Sage Sciences, Beverly, Mass.). The sequencing primer was annealed to the selected SMRT bell templates. The libraries were bound to DNA polymerase and loaded on the PacBio RSII for sequencing. Sequencing was completed using either C2/P4 or C3/P5 chemistry and 3-h movies. 8 SMRT cells of sequencing data were assembled with FALCON, version 0.2.2. The final assembly includes 29 contigs with an assembled genome size of 14.4 Mbp. Estimated fold coverage of the PacBio reads was 270λ.

Genome annotation was performed using the BRAKER (v2) training and annotation pipeline utilizing the 6 sets of transcriptomic reads (described below) to inform AUGUSTUS gene models. Functional annotation of the 8,902 genes was performed by InterProScan 5 and BLASTp serarches against the UniProt protein blast database. The P. renovo genome assembly and annotation is available for download at the Greenhouse Knowledgebase (greenhouse.lanl.gov).

Transcriptome Response to Salinity

In order to identify genes putatively conferring halotolerance, cells were cultivated under low- and high-salinity conditions, corresponding to 8.75 g/L and 35 g/L sea salts. Cells grow at approximately the same growth rate under these conditions (see FIG. 3C). Cells adapted to the appropriate salinity level were grown in NM2 medium, utilizing ammonium bicarbonate as a nitrogen source. Biological triplicate culture conditions were as follows: 33° C., 400 μmol m$^{-2}$ s$^{-1}$ lighting, and 2% constant CO$_2$ sparging in 100 mL volume. Seawater was employed as a source of salt, as this provides a more accurate proxy for halo-responsiveness compared to NaCl. Seawater was diluted with distilled water to obtain appropriate salinity levels. The data from these methods are reflected in FIG. 3C and salinity transcriptomics data. The above methods were done with the explicit goal of reducing culture shock, and subsequent global stress response, thus allowing a steady state comparison of RNA transcripts to salinity tolerance. RNA was obtained utilizing a QIAGEN RNeasy Plant Mini Kit following the manufacturer's recommendations, cells were homogenized under liquid nitrogen using a mortar and pestle. Paired-end 150 bp Illumina read RNA seq data were received from Genewiz in the form of compressed fastq files. Samples were comprised of 2 conditions and 3 biological replicates of each condition, resulting in 6 total samples. Raw fastq reads were quality trimmed using HTStream and mapped via Salmon to the available genomic assembly. Coding regions were extracted from the full reference assembly prior to mapping. Read counts were formatted into a tab-separated file and migrated to R to perform differential expression using the edgeR package. Low-level transcripts were filtered and removed, and all libraries were normalized to each other. Transcript counts were fit to a generalized linear model and the Cox-Reid profile-adjusted likelihood method was used to estimate the dispersion of each transcript. Differential expression was performed by a quasi-likelihood test between each condition. Transcripts were determined as differentially expressed when the corrected p-value (also known as q-value, or False Discover Rate) was less than or equal to 0.05 after a Benjamin-Hochberg correction for multiple hypothesis testing.

Whole genome alignments to other publicly available *Picochlorum* genomes were done as follows: 6 assemblies of different strains of *Picochlorums* sp. were compared using the nucmer utility in the large-scale alignment program MUMmer. Maximal matches were found and total bases matching between the samples were summed and the percent identity was reported as the average identity among the maximal unique matches.

Gene ontology analysis was performed as follows: differentially expressed genes were assigned putative functions by extracting the FASTA sequence from the original list of genes and aligning the sequence against the available *Chlamydomonas reinhardtii* annotated assembly (version 5.5) via BLAST. Protein identification numbers and putative annotations were the uploaded to the UniProt database and cross-referenced against the available gene ontology (GO) terms. GO terms were visualized on a semantic space scatterplot with the online software Revigo.

Nuclear Engineering

A nuclear integration cassette, as depicted in FIG. 7A, was synthesized and subcloned into the pUC19 plasmid backbone by Genewiz, Inc. The selection marker, 2A peptide and mCherry were codon optimized to the *P. renovo* genome. The final linear PR product (from primers PRD 49 and 11) for transformation was generated utilizing Q5 2× hot start master mix (NEB) and purified with a PureLink Quick PCR Purification kit (Invitrogen) following the manufacture's protocol, modified to include a second was step.

10 OD units (475×10$^6$ cells) of early log phase cells per transformation were harvested and washed 3 times at room temperature in 375 mM D-Sorbitol (Sigma S6021). Washing utilized 2 mL Eppendorf tubes, 950 µL of 375 mM D-Sorbitol per wash, centrifuged at 8000 g for 1 min. After washing, cells were resuspended in 100 µL of 375 mM D-Sorbitol; 3 g of DNA at 850 ng/µL (concentrated on a vacuum centrifuge) was added to the cells and gently mixed. Cells and DNA were incubated for 3 minutes, transferred to an ice cold 2 mm gap electroporation cuvette (Bulldog Bio) and electroporated with a Gene Pulser Xcell (Bio-Rad) electroporator utilizing a set time constant and voltage protocol of 2200 volts with a 25 ms time constant. Immediately following the pulse, cells were transferred to 400 µL of media supernatant (from the above utilized cells) and incubated at room temperature for 15 min. Cells were then split equally between 3 selection plates (1.5% agarose) comprised of NM2 supplemented with 20 µg/mL of phleomycin (InvivoGen). Plates were placed in a Percival incubator with fluorescent lighting at 33° C., 150 µmol m$^{-2}$ s$^{-1}$, and 1.5% $CO_2$. Colonies were counted and picked after 5 days for further analysis. A table of all DNA fragments and PCR primers utilized in this study is in Table 3.

Chloroplast Engineering

Homology arm sequences were PCR amplified from chloroplast genomic DNA using NEB Q5 Master Mix from New England Biolabs. A promoter-RBS-sfGFP-RBS-ereB-terminator cassette was synthesized by Genewiz, Inc as depicted in FIG. 8A. The chloroplast integration cassette was assembled into a pUC19 backbone using 2× Gilson Assembly Mix from New England Biolabs, following the manufacturer's protocol. Complete vector sequences were confirmed by Sanger sequence analysis (Genewiz).

Biolistic transformation was employed to deliver DNA into the chloroplast, as reported previously. 10 µg of plasmid DNA (QIAprep spin miniprep kit QIAGEN) was precipitated onto 550 nm gold sphere nanoparticles (Seashell Inc.) under constant vortexing. 10 µL of plasmid DNA (1 µg/µL) was added to 60 µL of gold particles (50 mg/ml), followed by dropwise addition of 50 L of 2.5 M $CaCl_2$) and 20 µL of 0.1 M spermidine (Sigma 50266-1G). This was vortexed for 5 min, incubated for 1 min at room temperature, briefly centrifuged, and washed with 140 µL of isopropanol.

Following removal of wash supernatant, the gold particles were resuspended in 60 µL of isopropanol and gently sonicated in a bath sonicator to resuspend the pellet. To assay loading efficiency of the DNA onto the gold, a 9 µL aliquot was taken, washed in 9 µL of water and assayed for DNA concentration utilizing a NanoDrop 2000 spectrophotometer.

To transform *P. renovo*, an overnight culture was grown to early log phase in NM2, concentrated to 2.5 OD units in 170 µL, and spread evenly onto a 100×15 mm NM2 agar plate supplemented with 800 µg/mL erythromycin (Sigma E5389-5G). A Biolistic PDS-1000/He Particle Delivery System (metal case version) (Bio-Rad) was used for bombardment, which was accomplished by drying 9 µL of the above DNA loaded gold particles onto the marcocarrier (fast, low humidity drying was accomplished by placing the loaded microcarrier into the bombardment chamber and pulling vacuum), and bombarding cells 5 cm below the microcarrier with a 1100 psi rupture disk. After bombardment, plates were placed into the same growth conditions described above. Following 7 days of growth, the plates were imaged with a FluoroChemQ gel imaging station (Protein Simple) with 475/35 and 573/35 nm respective excitation and emission filters, which allowed direct imaging of sfGFP positive colonies.

To assess construct integration into the genomes of *P. renovo*, genomic DNA was extracted utilizing a MasterPure™ Yeast DNA Purification kid (Lucigen). PCR was performed utilizing Q5 Hot Start High-Fidelity polymerase (New England Biolabs) according to the manufacturer's recommendations. A table of the utilized primers is provided in Table 3.

Fluorescent Plate Reader Analysis

Colonies were restreaked onto fresh agar plates supplemented with the appropriate selection marker (phleomycin 20 µg/mL and erythromycin 800 µg/mL for the nucleus and chloroplast, respectively) and grown in triplicate in 3 mL of growth media (no selection marker) in standard glass cell culture tubes mixed daily via vortexing. Cultures were grown in the above described Percival incubator conditions (33° C., 150 µmol ma s$^2$, 1.5% $CO_2$). Early log phase cells were analyzed for mCherry and sfGFP fluorescence utilizing 200 µL of cell culture in a black 96 well plate and a FLUOstar Omega plate reader v. 5.11 R3 (BMG Labtech). To quantify mCherry a 584 nm excitation filter and 620/10 nm emission filter were utilized with gain set to 2500; to quantify sfGFP a 485/12 nm excitation and 520 nm emission filter set was used with gain set to 1200. Data was normalized to chlorophyll content, which was determined by using a 485/12 nm excitation and 680/10 emission filters, with gain set to 1500. Data is represented as a fold increase over the wild type alga.

Microscopy

Mid-log phase chloroplast sfGFP transformants and wild type were imaged with a Nikon Eclipse 80i microscope, equipped with a Nikon Intensilight C-HGFI mercury lamp light source, a Nikon Plan Apo VC 100× objective lens, and a Nikon DS-QiMc camera. NIS-Elements BR 4.30.01 software was utilized for imaging chlorophyll and sfGFP (31017—Chlorophyll Bandpass Emission and 41017—Endow GFP/EGFP Bandpass, both from CHORMA®). Imaging of wild type and transgenic lines employed equivalent exposure time and gain settings. ImageJ was used for post imaging analysis.

Nuclear mCherry transformants and wild type were imaged with a Nikon C1si confocal microscope, equipped with EZ-C1 3.60 software. Chlorophyll was imaged with a 650 LP filter. mCherry was imaged with a 590/50 filter. Both chlorophyll and mCherry were excited with an 561.4 nm laser. Laser intensity, pin hole size, pixel dwell time, and gain were set using an mCherry clone. Equivalent settings were utilized for imaging wild type cells. ImageJ was used for post imaging analysis.

The foregoing disclosure includes various examples set forth merely as illustration. The disclosed examples are not intended to be limiting. Modifications incorporating the spirit and substance of the described examples may occur to persons skilled in the art. These and other examples are within the scope of this disclosure and the following claims.

The invention claimed is:

1. A method for transforming a *Picochlorum renovo* algal chloroplast, the method comprising:
   introducing an exogenous selection marker into the *Picochlorum renovo* algal chloroplast; and
   bombarding a culture of the *Picochlorum renovo* algal chloroplast with a loaded particle.

2. A method for transforming a *Picochlorum renovo* algal nucleus, the method comprising:
   synthesizing a nuclear integration cassette;
   integrating the nuclear integration cassette into a plasmid backbone; and
   codon optimizing a gene encoding a selection marker and a gene encoding a peptide into a genome of the *Picochlorum renovo* algal nucleus;
   bombarding a culture of the *Picochlorum renovo* algal nucleus with a loaded particle.

3. The method of claim 2, wherein the selection marker encodes for resistance to erythromycin.

4. The method of claim 2, wherein the plasmid backbone is pUC19.

5. The method of claim 2, wherein the peptide is a 2A peptide.

6. The method of claim 2, wherein the loaded particle comprises:
   a gold sphere nanoparticle,
   plasmid DNA precipitated onto the gold sphere nanoparticle, and
   spermidine.

7. The method of claim 1, wherein the selection marker encodes for resistance to erythromycin.

8. The method of claim 1, wherein the loaded particle comprises:
   a gold sphere nanoparticle,
   plasmid DNA precipitated onto the gold sphere nanoparticle, and
   spermidine.

* * * * *